(12) United States Patent
Zheng et al.

(10) Patent No.: US 12,203,101 B2
(45) Date of Patent: Jan. 21, 2025

(54) THERMOSTABLE GLUCOSE OXIDASE

(71) Applicant: NANJING BESTZYME BIO-ENGINEERING CO., LTD., Jiangsu (CN)

(72) Inventors: Fei Zheng, Jiangsu (CN); Ting Yan, Jiangsu (CN); Jidong Zhu, Jiangsu (CN); Hong Xu, Jiangsu (CN); Yan Sun, Jiangsu (CN); Aixi Bai, Jiangsu (CN)

(73) Assignee: NANJING BESTZYME BIO-ENGINEERING CO., LTD., Jiangsu (CN)

( * ) Notice: Subject to any disclaimer, the term of this patent is extended or adjusted under 35 U.S.C. 154(b) by 453 days.

(21) Appl. No.: 17/615,342

(22) PCT Filed: May 29, 2020

(86) PCT No.: PCT/CN2020/093205
§ 371 (c)(1),
(2) Date: Nov. 30, 2021

(87) PCT Pub. No.: WO2020/239064
PCT Pub. Date: Dec. 3, 2020

(65) Prior Publication Data
US 2022/0220454 A1    Jul. 14, 2022

(30) Foreign Application Priority Data
May 31, 2019    (CN) .................. 201910469009.X

(51) Int. Cl.
| | |
|---|---|
| *C12N 9/04* | (2006.01) |
| *C12N 15/82* | (2006.01) |
| *C12R 1/66* | (2006.01) |
| *C12R 1/84* | (2006.01) |

(52) U.S. Cl.
CPC ........... *C12N 9/0006* (2013.01); *C12N 15/82* (2013.01); *C12R 2001/66* (2021.05); *C12R 2001/84* (2021.05); *C12Y 101/03004* (2013.01)

(58) Field of Classification Search
CPC .. C12N 9/0006; C12N 15/82; C12N 2001/66; C12N 2001/84; C12N 15/815; C12Y 101/03004
See application file for complete search history.

(56) References Cited

FOREIGN PATENT DOCUMENTS

| | | | | |
|---|---|---|---|---|
| CN | 1238009 | A | 12/1999 | |
| CN | 107858338 | A | 3/2018 | |
| CN | 108795891 | A | 11/2018 | |
| CN | 108913675 | A | 11/2018 | |
| CN | 109666657 | A | 4/2019 | |
| CN | 109706137 | A | 5/2019 | |
| DE | 2796547 | A1 * | 10/2014 | ............... C12N 9/04 |
| WO | WO 9803639 | A1 * | 1/1998 | ............... C12N 9/34 |

OTHER PUBLICATIONS

Chinese Application No. 202080039321.6, Office Action dated Nov. 6, 2023.
GenBank Accession No. P13006; Genbank Database, May 1, 1992; 5 pgs.

* cited by examiner

*Primary Examiner* — Satyendra K Singh
(74) *Attorney, Agent, or Firm* — Tarolli, Sundheim, Covell & Tummino LLP

(57) ABSTRACT

Provided is a thermostable glucose oxidase obtained by introducing at least one pair of disulfide bonds into an amino acid sequence of a wild-type *Aspergillus niger* glucose oxidase or a mutant *Aspergillus niger* glucose oxidase. The glucose oxidase is suitable for application in the fields of food, chemical engineering, medicine, agriculture and feeds.

17 Claims, 2 Drawing Sheets
Specification includes a Sequence Listing.

THERMOSTABLE GLUCOSE OXIDASE

TECHNICAL FIELD

The present invention belongs to the field of protein engineering, and specifically relates to a glucose oxidase derived from filamentous fungi, especially an *Aspergillus niger* glucose oxidase. The thermal stability of the *Aspergillus niger* glucose oxidase is improved after modification by introducing disulfide bonds.

BACKGROUND

A glucose oxidase (GOD, E.C 1.1.3.4) is an aerobic dehydrogenase, its enzyme molecule is a dimer containing two subunits and having a molecular weight of about 160 kDa, and each subunit is combined with an FAD molecule. The glucose oxidase can be used for specifically catalyzing β-D-glucose to produce gluconic acid and hydrogen peroxide by using molecular oxygen as an electron acceptor. GOD is widely distributed in animals, plants and microorganisms, but there are certain limitations in extracting GOD from animal and plant tissues, the enzyme production is not high, and the GOD production of bacteria is also low. A microbial fermentation method is a main method for producing GOD. At present, most of commercial products on the market are produced by fermenting *Pichia pastoris* and filamentous fungi, such as *Aspergillus niger* and *Aspergillus oryzae*.

Due to the advantages of catalytic specificity and high efficiency, GOD is widely used in the fields of food, chemical engineering, medicine, agriculture and feeds and has received more and more attention in recent years, and market demands are also increasing. Due to the effects of deoxidation and oxidation resistance, GOD is widely used in the fields of food, medicine and feeds. As a food preservative in the food industry, GOD has significant effects in preventing aging of beers, maintaining original flavors of products and prolonging the shelf life and can also be used as a flour improver and a bread quality improver to improve food quality. In the medical field, a GOD electrode method and a GOD-peroxidase coupling method are commonly used to detect the content of glucose in blood and serum. As a new feed additive, GOD can improve intestinal environments of animals, so that the feed utilization rate is increased, and the growth of the animals is promoted. Since GOD is widely used in various fields, higher and higher requirements are put forward for existing performance of the GOD in industry, especially the feed industry. For example, the enzyme activity is not reduced at room temperature for a long time, and the GOD has resistance to heat, extreme pH conditions and digestive enzymes. The thermal stability is very important in application of GOD, and GOD with high heat resistance has higher advantages in preparation of GOD under extreme reaction conditions (high temperature). Therefore, improvement of the thermal stability of GOD has an important practical significance in wide promotion and application of the GOD.

SUMMARY

The inventor found that the stability can be improved by introducing one or more pairs of disulfide bonds to specific positions in an amino acid sequence of a wild-type *Aspergillus niger* glucose oxidase (for example, those having sequence identity higher than 80% with a wild-type *Aspergillus niger* glucose oxidase set forth in SEQ ID NO: 1) or a mutant *Aspergillus niger* glucose oxidase (for example, those having sequence identity higher than 75% with a mutant *Aspergillus niger* glucose oxidase set forth in SEQ ID NO: 8 or SEQ ID NO: 10).

In some embodiments, one or more pairs of disulfide bonds shown in Table 1 are introduced to specific positions in an amino acid sequence of a mutant *Aspergillus niger* glucose oxidase having sequence identity higher than 80% with the wild-type *Aspergillus niger* glucose oxidase set forth in SEQ ID NO: 1. In some preferred embodiments, one or more pairs of disulfide bonds shown in Table 1 are introduced to specific positions in an amino acid sequence of an *Aspergillus niger* glucose oxidase having sequence identity higher than 85%, 88%, 89%, 90%, 91%, 92%, 93%, 94%, 95%, 96%, 97%, 98% or 99% with the wild-type *Aspergillus niger* glucose oxidase set forth in SEQ ID NO: 1.

In other embodiments, one or more pairs of disulfide bonds shown in Table 1 are introduced to specific positions in an amino acid sequence of a mutant *Aspergillus niger* glucose oxidase having sequence identity higher than 75% with the mutant *Aspergillus niger* glucose oxidase set forth in SEQ ID NO: 8 or SEQ ID NO: 10. In some preferred embodiments, one or more pairs of disulfide bonds shown in Table 1 are introduced to specific positions in an amino acid sequence of a mutant *Aspergillus niger* glucose oxidase having sequence identity higher than 78%, 79%, 80%, 82%, 84%, 86%, 88%, 90%, 91%, 92%, 93%, 94%, 95%, 96%, 97%, 98% or 99% with the mutant *Aspergillus niger* glucose oxidase set forth in SEQ ID NO: 8 or SEQ ID NO: 10.

Specifically, the inventor found that the thermal stability can be improved by separately introducing one pair or a combination of more pairs of disulfide bonds in Table 1 one or more pairs of disulfide bonds shown in Table 1 are introduced the *Aspergillus niger* glucose oxidase mutant set forth in SEQ ID NO: 8 or SEQ ID NO: 10.

TABLE 1

Names and positions of introduced disulfide bonds (the amino acid position number is based on SEQ ID NO: 1)

| Names of disulfide bonds | Positions of disulfide bonds |
| --- | --- |
| A | S53/T246 |
| B | A25/V250 |
| C | V20/S45 |
| D | T39/L242 |
| E | T87/P508 |

In order to achieve an objective of the present invention, "introduction" does not limit formation of the disulfide bonds to any particular way. For example, "introduction" of the disulfide bonds may include replacing an amino acid residue at a corresponding position in a glucose oxidase sequence into which the disulfide bonds are to be introduced with an amino acid residue capable of forming disulfide bonds (including, for example, a cysteine residue Cys, a homocysteine residue Hcy, and the like) and/or inserting an amino acid residue capable of forming disulfide bonds at a corresponding position. Such substitution and/or insertion may be achieved, for example, by using a site-directed mutagenesis method known in the art. "Introduction" also includes the situation that any one or two amino acid residues forming the disulfide bonds are produced by natural mutation. In order to produce such modified mutants, microbial bacteria such as *Escherichia coli*, fungi such as yeast (*Pichia pastoris, Schizosaccharomyces pombe* and the like), filamentous fungi (such as *Aspergillus niger, Aspergillus*

*oryzae* and *Trichoderma reesei*) and plants (such as corn, soybeans and wheat) can be used as hosts for expression.

In order to construct the mutants above, a conventional site-directed mutagenesis method can be used on the basis of a wild-type nucleic acid sequence, and a gene synthesis method can also be used for synthesizing the mutants from zero. A promoter and a terminator are ligated, introduced into a host cell and then expressed under suitable culture conditions. The methods above are conventional methods in the art.

Based on this discovery, this application provides the following technical solutions.

An objective of the present invention is to provide a thermostable glucose oxidase, containing at least one pair of introduced disulfide bonds in an amino acid sequence of a wild-type *Aspergillus niger* glucose oxidase or a mutant *Aspergillus niger* glucose oxidase, where the amino acid sequence of the wild-type glucose oxidase is set forth in SEQ ID NO: 1; compared with the wild-type *Aspergillus niger* glucose oxidase set forth in SEQ ID NO: 1, the mutant *Aspergillus niger* glucose oxidase has mutants in at least one position; and the introduced disulfide bonds are selected from:

(A) disulfide bonds formed between an amino acid residue at a position corresponding position 53 of SEQ ID NO: 1 and an amino acid residue at a position corresponding to position 246 of SEQ ID NO: 1;

(B) disulfide bonds formed between an amino acid residue at a position corresponding position 25 of SEQ ID NO: 1 and an amino acid residue at a position corresponding to position 250 of SEQ ID NO: 1;

(C) disulfide bonds formed between an amino acid residue at a position corresponding position 20 of SEQ ID NO: 1 and an amino acid residue at a position corresponding to position 45 of SEQ ID NO: 1;

(D) disulfide bonds formed between an amino acid residue at a position corresponding to position 39 of SEQ ID NO: 1 and an amino acid residue at a position corresponding to position 242 of SEQ ID NO: 1;

(E) disulfide bonds formed between an amino acid residue at a position corresponding to position 87 of SEQ ID NO: 1 and an amino acid residue at a position corresponding to position 508 of SEQ ID NO: 1.

In some embodiments of the present invention, compared with the wild-type *Aspergillus niger* glucose oxidase set forth in SEQ ID NO: 1, the mutant *Aspergillus niger* glucose oxidase has mutants in at least one of the following positions: 14, 16, 25, 30, 34, 37, 43, 45, 53, 67, 84, 90, 92, 94, 96, 106, 121, 135, 141, 142, 162, 167, 204, 246, 259, 315, 332, 362, 405, 406, 420, 446, 449, 453, 477, 501, 504, 506, 509, 510, 521, 526, 528, 536, 554, 560, 572, 575 and 577.

In some embodiments of the present invention, compared with the wild-type *Aspergillus niger* glucose oxidase set forth in SEQ ID NO: 1, the mutant *Aspergillus niger* glucose oxidase has at least one of the following mutants: D14E, S16A, A25V, T30V, T34V, R37K, N43D, S45T, S53C, A67Y, E84C, Q90R, A92Q, I94V, S96F, V106I, S121A, N135S, L141K, Q142K, A162T, V167I, F204L, T246C, G259A, D315K, A332S, S362T, N405K, H406D, V420E, H446R, A449M, Q453N, S477Y, S501R, T504V, Y506W, Y509E, H510N, C521A, K526R, M528L, A536L, T554M, V560L, S572A, I575V and E577A.

In some embodiments of the present invention, compared with the wild-type *Aspergillus niger* glucose oxidase set forth in SEQ ID NO: 1, the mutant *Aspergillus niger* glucose oxidase has mutants in at least one of the following positions: 14, 16, 30, 34, 37, 43, 45, 53, 67, 84, 90, 94, 106, 135, 162, 167, 204, 246, 259, 315, 332, 362, 405, 406, 420, 446, 501, 504, 509, 510, 554, 572, 575 and 577.

In some embodiments of the present invention, compared with the wild-type *Aspergillus niger* glucose oxidase set forth in SEQ ID NO: 1, the mutant *Aspergillus niger* glucose oxidase has at least one of the following mutants: D14E, S16A, T30V, T34V, R37K, N43D, S45T, S53C, A67Y, E84C, Q90R, I94V, V106I, N135S, A162T, V167I, F204L, T246C, G259A, D315K, A332S, S362T, N405K, H406D, V420E, H446R, S501R, T504V, Y509E, H510N, T554M, S572A, I575V and E577A.

In some embodiments of the present invention, compared with the wild-type *Aspergillus niger* glucose oxidase set forth in SEQ ID NO: 1, the mutant *Aspergillus niger* glucose oxidase has mutants in at least one of the following positions: 14, 30, 37, 43, 45, 53, 67, 84, 90, 94, 106, 135, 162, 167, 204, 246, 259, 315, 406, 420, 446, 501, 509, 572 and 577.

In some embodiments of the present invention, compared with the wild-type *Aspergillus niger* glucose oxidase set forth in SEQ ID NO: 1, the mutant *Aspergillus niger* glucose oxidase has at least one of the following mutants: D14E, T30V, R37K, N43D, S45T, S53C, A67Y, E84C, Q90R, I94V, V106I, N135S, A162T, V167I, F204L, T246C, G259A, D315K, H406D, V420E, H446R, S501R, Y509E, S572A and E577A.

In some embodiments of the present invention, compared with the wild-type *Aspergillus niger* glucose oxidase set forth in SEQ ID NO: 1, the mutant *Aspergillus niger* glucose oxidase has mutants in at least one of the following positions: 14, 30, 37, 43, 53, 67, 84, 90, 94, 106, 135, 162, 204, 246, 315, 446, 501, 509 and 554.

In some embodiments of the present invention, compared with the wild-type *Aspergillus niger* glucose oxidase set forth in SEQ ID NO: 1, the mutant *Aspergillus niger* glucose oxidase has at least one of the following mutants: D14E, T30V, R37K, N43D, S53C, A67Y, E84C, Q90R, I94V, V106I, N135S, A162T, F204L, T246C, D315K, H446R, S501R, Y509E and T554M.

In some embodiments of the present invention, the amino acid sequence of the mutant *Aspergillus niger* glucose oxidase is set forth in SEQ ID NO. 8 or SEQ ID NO. 10.

In some embodiments of the present invention, the amino acid sequence of the thermostable glucose oxidase satisfies at least one of the items (A), (B), (C) and (E).

In some embodiments of the present invention, the amino acid sequence of the thermostable glucose oxidase satisfies any two, three or all of the items (A), (B), (C) and (E).

In some embodiments of the present invention, the amino acid sequence of the thermostable glucose oxidase satisfies the item (A), (B) or (C).

In some embodiments of the present invention, the amino acid sequence of the thermostable glucose oxidase satisfies the item (A).

In some embodiments of the present invention, the amino acid sequence of the thermostable glucose oxidase satisfies the item (B).

In some embodiments of the present invention, the amino acid sequence of the thermostable glucose oxidase satisfies the item (C).

In some embodiments of the present invention, the thermostable glucose oxidase includes any amino acid sequence selected from the following group consisting of SEQ ID NOs: 11-15, 17, 19, 21 or 23.

In some embodiments of the present invention, the thermostable glucose oxidase is obtained by heterologous expression in a *Pichia pastoris* host.

In some embodiments of the present invention, the amino acid residue capable of forming the disulfide bonds is a cysteine residue or a homocysteine residue.

Another objective of the present invention is to provide a polynucleotide encoding the thermostable glucose oxidase.

In some embodiments of the present invention, a sequence of the polynucleotide encoding the thermostable glucose oxidase is codon-optimized for expression in *Pichia pastoris*.

In some embodiments of the present invention, the polynucleotide includes a nucleotide sequence set forth in any one of SEQ ID NO: 3-7, 16, 18, 20 or 22.

Another objective of the present invention is to provide a host cell, which contains the polynucleotide encoding the thermostable glucose oxidase.

In some embodiments of the present invention, the host cell is a fungal cell, a bacterial cell or a plant cell.

In some embodiments of the present invention, the host cell is a yeast cell or a filamentous fungal cell.

In some embodiments of the present invention, the host cell is a *Pichia pastoris* cell or an *Aspergillus niger* cell.

A fourth objective of the present invention is to provide application of the thermostable glucose oxidase in the fields of food, chemical engineering, medicine, agriculture or feeds.

As used herein, A, R, C, Q, N, L, K, M, F, P, S, T, W, Y, V, G and E are abbreviations of alanine (Ala), arginine (Arg), cysteine (Cys), glutamine (Gln), asparagine (Asn), leucine (Leu), lysine (Lys), methionine (Met), phenylalanine (Phe), proline (Pro), serine (Ser), threonine (Thr), tryptophan (Trp), tyrosine (Tyr), valine (Val), glycine (Gly) and glutamic acid (Glu) respectively.

As used herein, the term "glucose oxidase mutant", "mutant" or "mutant glucose oxidase" refers to a polypeptide having glucose oxidase activity and comprising a change such as substitution, insertion and/or deletion of one or more (several) amino acid residues at one or more (several) positions. Substitution refers to replacing an amino acid at a certain position with a different amino acid; deletion refers to removing an amino acid at a certain position; insertion refers to adding 1-5 amino acids to a position adjacent to and behind an amino acid at a certain position. Mutation of the wild-type glucose oxidase also refers to substitution, insertion and/or deletion of an amino acid in at least one position compared with the wild-type glucose oxidase, and preferably refers to substitution of an amino acid in at least one position; for example, T30V refers to substitution of threonine at the position 30 in the wild-type glucose oxidase with valine.

As used herein, the term "thermal stability" means that certain enzyme activity of the glucose oxidase mutant of the present invention is still maintained at a specific temperature after a given period of time. When properties such as thermal stability are involved, the term "improved thermal stability" means that after a period of time, the enzyme activity of the glucose oxidase mutant is higher than that of other glucose oxidase mutants and/or wild-type glucose oxidases.

As used herein, the terms "polynucleotide" and "nucleic acid" can be used interchangeably and refer to a polymerization form of nucleotides including ribonucleotides or deoxyribonucleotides in any length. Such terms include but are not limited to single-stranded, double-stranded or triple-stranded DNA, genomic DNA, cDNA, RNA, DNA-RNA hybrids or polymers containing purines, pyrimidine bases or other naturally, chemically or biochemically modified, non-nature or derived nucleotide bases.

As used herein, the term "vector" refers to a polynucleotide construct designed to introduce nucleic acid into one or more cell types. The vector includes a cloning vector, an expression vector, a shuttle vector, a plasmid, a kit and the like.

As used herein, the term "gene" refers to a polynucleotide encoding a polypeptide, including regions before and after a coding region and an intervening sequence (an intron) located between individual coding segments (exons).

As used herein, the term "percent (%) sequence identity" is defined as the percentage of amino acid residues in a candidate sequence the same as amino acid residues in a specific peptide or polypeptide sequence after the sequences are compared, gaps are introduced when necessary to obtain the maximum percent sequence identity and any conservative substitutions are not taken as a part of the sequence identity. Sequence comparisons can be performed in various ways within the technical scope of the field to determine percent amino acid sequence identity. For example, publicly available computer software, such as BLAST, BLAST-2, ALIGN or Megalign (DNASTAR) software is used. Those skilled in the art can determine appropriate parameters for measuring comparison, including any algorithm required to obtain the maximum comparison over the full length of the compared sequences.

As used herein, the term "host cell" refers to a host suitable for an expression vector containing the DNA according to the present invention.

The present invention has the following beneficial effects:

In the present invention, one or more pairs of disulfide bonds are introduced into a wild-type glucose oxidase and treated at 70° C. for 3 minutes, and the thermal stability is significantly improved than that of the wild-type glucose oxidase. Preferably, the enzyme activity of the glucose oxidase mutant is improved by 70% or above. More preferably, the enzyme activity of the glucose oxidase mutant is improved by 120% or above. Particularly preferably, the enzyme activity of the glucose oxidase mutant is improved by 180%. In the present invention, one or more pairs of disulfide bonds are introduced into the glucose oxidase mutant and treated at 70° C. for 3 minutes, and the enzyme activity is improved by 34% or above than that of the mutant. After treatment at 80° C. for 3 minutes, the enzyme activity is greatly improved from zero. In the present invention, one or more pairs of disulfide bonds are introduced into a glucose oxidase mutant derived from other *Aspergillus niger* and treated at 80° C. for 3 minutes, and the enzyme activity is improved by 350% or above than that of the mutant and is significantly higher than that of the existing wild-type glucose oxidase. Therefore, according to the technical solutions of the present invention, the enzyme activity of the glucose oxidase can be improved. Especially, due to the thermal stability, the glucose oxidase is suitable for application in industrial production, for example, application in the fields of food, chemical engineering, medicine, agriculture, and feeds.

DETAILED DESCRIPTION

Technical solutions of the present invention are further described in detail below with reference to the specific examples. It should be noted that, the examples described herein are merely used for explaining the present invention, instead limiting the scope of the present invention.

Example 1 Construction of Disulfide Bond Mutants

The 3D structure of a wild-type *Aspergillus niger* glucose oxidase is published (see Wohlfahrt, G et al, (1999) Acta Crystallogr., Sect. D55: 969-977), a 3D structure file PDB ID 1CF3 is taken as a reference, and disulfide bonds shown in the following table are designed and introduced.

TABLE 2

Names and positions of introduced disulfide bonds (the amino acid position number is based on SEQ ID NO: 1)

| Names of disulfide bonds | Positions of disulfide bonds |
| --- | --- |
| A | S53C/T246C |
| B | A25C/V250C |
| C | V20C/S45C |
| D | T39C/L242C |
| E | T87C/P508C |
| F | L9C/L245C |
| G | G52C/G99C |
| H | S56C/R230C |
| I | S45C/N241C |
| J | E63C/V224C |
| K | Y182C/G346C |
| L | G251C/P443C |
| M | S191C/A479C |

Figure 1:
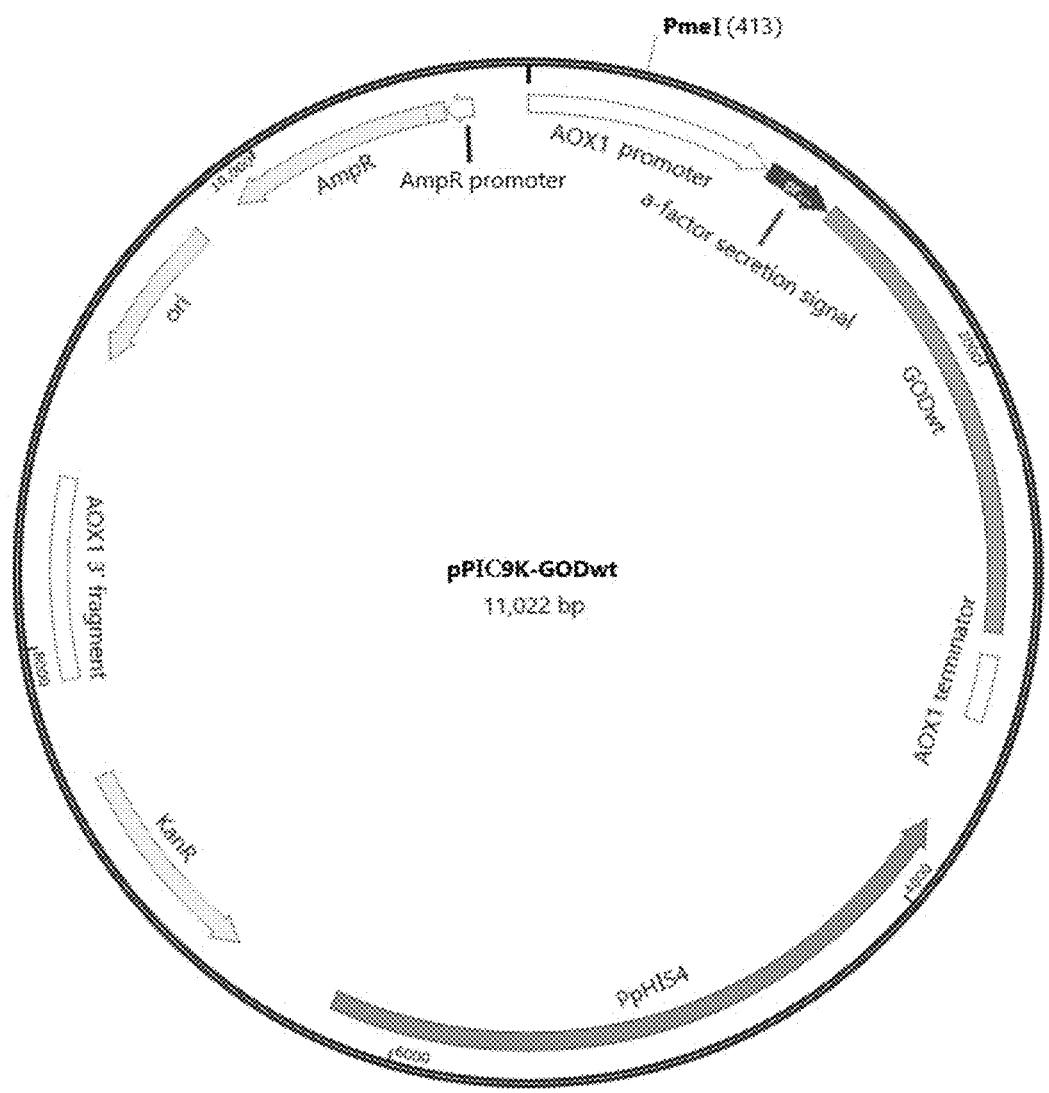
FIG. 1 is a pPIC9K-GOD-wt plasmid profile.

The amino acid sequence of the wild-type glucose oxidase was set forth in SEQ ID NO: 1, pPIC9K was used as an expression vector, a *Saccharomyces cerevisiae* Alpha factor was used as a signal peptide, a synthetic wild-type glucose oxidase gene sequence GOD-wt (the sequence contains EcoR I and Not I digestion sites at two ends) and pPIC9K were digested with EcoR I and Not I respectively and then ligated and transferred into *Escherichia coli* DH5 α competent cells, transformants were picked for sequencing verification, and a wild-type glucose oxidase expression plasmid pPIC9K-GOD-wt shown in FIG. 1 was obtained. Mutant sequences were named GOD-A to GOD-M according to names of the disulfide bonds in the table above. A glucose oxidase gene GOD-wt (set forth in SEQ ID NO: 2) and the mutant sequences GOD-A to GOD-M were synthesized by using a whole gene synthesis method, the mutant sequences GOD-A to GOD-E were set forth in SEQ ID NO: 3 to SEQ ID NO: 7, and gene synthesis was completed by Nanjing GenScript Biotechnology Co., Ltd. The synthetic gene have EcoR I and Not I restriction sites at two ends.

In order to express the glucose oxidase and the mutants, operations were performed on *Pichia pastoris* GS115 and the plasmid with reference to instructions of a Pichia expression kit (Invitrogen). Specifically, after the *Pichia pastoris* GS115 strain was cultured on a YPD culture plate (1% yeast extract, 2% proteins, 2% glucose and 1.5% agar) at 30° C. for 48 hours, single clones were picked and cultured in 4 mL of a YPD liquid culture medium (1% yeast extract, 2% proteins, and 2% glucose) at 30° C. and 200 rpm for 12 hours and then transferred into a triangular flask containing 30 mL of a YPD liquid culture medium and cultured at 30° C. and 220 rpm for 4-5 hours, the culture solution was centrifuged at 4° C. and 9,000 rpm for 2 minutes after it was detected that the OD600 value was in a range of 1.1-1.3, 4 mL of bacterial cells were collected into a sterilized EP tube, a supernatant was slightly removed, the remaining supernatant was absorbed with sterilized filter paper, the bacterial cells were resuspended in 1 mL of precooled sterilized water and centrifuged at 4° C., and 9,000 rpm for 2 minutes, and the supernatant was removed. The steps above were repeated, the bacterial cells were resuspended in 1 mL of precooled sorbitol (1 mol/L) and centrifuged at 4° C. and 9,000 rpm for 2 minutes, the supernatant was removed, and the bacterial cells were resuspended in 100-150 μl of precooled sorbitol (1 mol/L) to prepare competent cells. The expression plasmid pPIC9K-GOD-wt and the remaining 13 disulfide bond mutants were linearized with PmeI, linearized fragments were purified, recovered and then transferred into the *Pichia pastoris* GS115 competent cells by using an electroporation method, a mixture was uniformly coated on an MDH plate and invert-cultured at 30° C. for 2-3 days, all colonies on the plate were washed off with sterile water and then coated on YPD plates (0.5-8 mg/mL) containing different concentrations of geneticin, and multi-copy transformants were screened. Recombinant *Pichia pastoris* strains screened on the MDH plate were named GOD-A, GOD-B, GOD-C, GOD-D, GOD-E, GOD-F, GOD-G, GOD-H, GOD-I, GOD-J, GOD-K, GOD-L and GOD-M. The clones obtained after screening were separately transferred into a BMGY culture medium and cultured in an oscillating shaker at 30° C. and 250 rpm for 24 hours, then transferred into a BMMY culture medium for induced expression at 30° C. and 250 rpm for 120 hours with addition of 0.5% methanol every day, and finally centrifuged at 9,000-12,000 rpm for 10 minutes to remove the bacterial cells, a fermentation supernatant containing the glucose oxidase GOD-wt and 13 mutants thereof was obtained, and SDS-PAGE results show that GOD-G, GOD-I, GOD-K and GOD-L mutants were not expressed and the remaining 9 mutants were all expressed.

Example 2 Detection of Enzyme Activity of Glucose Oxidase

Under aerobic conditions, dehydrogenation of glucose was catalyzed by GOD to produce H2O2, and under the action of a horseradish peroxidase (POD), an oxygen donor o-dianisidine (DH2) was oxidized to obtain a brown product. The activity of GOD can be calculated according to a change of an absorbance at 540 nm and a standard curve. An enzyme activity determination system containing 2.5 mL of an o-dianisidine solution, 0.3 mL of 18% glucose and 0.1 mL of a 90 U/mL horseradish peroxidase was kept at 35° C. for 2 minutes, 0.1 mL of a diluted enzyme solution sample was added into a test tube for reaction for 3 minutes, 2 mol/L sulfuric acid was added to stop the reaction, the test tube was taken out, an absorbance at OD540 was determined, and a heat-inactivated enzyme solution was used as a blank control. According to results of the standard curve, an activity unit of the glucose oxidase was calculated.

Reagents and Solutions

A 0.1 mol/L disodium hydrogen phosphate-sodium citrate buffer with a pH of 5.5:14.32 g of disodium hydrogen phosphate and 8.4056 g of citric acid monohydrate were accurately weighed and dissolved in 400 ml of distilled water, the pH was adjusted to 5.5 with disodium hydrogen phosphate, and the buffer was obtained for later use.

An o-dianisidine solution: 0.1 g of o-dianisidine was accurately weighed and dissolved in 10 ml of methanol to obtain a stock solution with effective storage time of 3 days at 4° C. Before an experiment, 0.1 ml of the stock solution was taken and dissolved in 12 ml of the 0.1 mol/L phosphate buffer with a pH of 5.5 to obtain the o-dianisidine solution.

18% glucose: 9.0000 g of glucose (AR) dried to a constant weight was accurately weighed and dissolved in a small amount of distilled water, and the solution was made to 50 ml with distilled water and stored at 4° C.

2 mol/L H2SO4:40.00 g of H2SO4 was accurately weighed and slowly added into 160 mL of distilled water, and the solution was made to 200 mL for later use.

A GOD standard product: a sigma glucose oxidase standard product with an enzyme activity of 10,000 units was purchased, 5 mL of distilled water was accurately added and mixed, and the solution was stored at −20° C. for later use.

A 90 U/mL horseradish peroxidase: a horseradish peroxidase standard product (enzyme activity>250 units/mg, 100 mg) was purchased, 1 mL of distilled water was accurately added to fully dissolve the horseradish peroxidase, and the solution was stored at −20° C. for later use. An appropriate amount of the standard product was taken and diluted to an enzyme activity of 90 U/ml before use, and the standard product needs to be used immediately after dilution.

Determination of Enzyme Activity (1) Drawing of a Standard Curve

GOD standard products were diluted to 0.4, 0.8, 1.2, 1.6, 2.0 and 2.4 U/mL respectively, 2.5 mL of the o-dianisidine solution, 0.3 mL of 18% glucose solution and 0.1 mL of the 90 U/mL horseradish peroxidase solution were added into a test tube and preheated at 35° C. for 2 minutes, 0.1 mL of the diluted GOD standard product was added at an interval of 15 seconds and accurately reacted for 3 minutes, then 2 ml of 2 mol/L H2SO4 was immediately added to stop the reaction, the mixture was taken out and mixed uniformly, an absorbance value at 540 nm was determined, and a standard curve y=Kx+b was drawn with the absorbance value as the abscissa and a standard enzyme activity as the ordinate.

(2) Determination of Samples 2.5 mL of the o-dianisidine solution, 0.3 mL of 18% glucose solution and 0.1 mL of the 90 U/mL horseradish peroxidase solution were added into a test tube and preheated at 35° C. for 2 minutes, 0.1 mL of a diluted to-be-detected sample (a dilution standard is that the detected absorbance of the sample was within a linear range) was added at an interval of 15 seconds and accurately subjected to a reaction for 3 minutes, 2 ml of 2 mol/L H2SO4 was immediately added to stop the reaction, the mixture was taken out and mixed uniformly, the absorbance value A at 540 nm was detected, and the enzyme activity was calculated.

(3) Calculation of Enzyme Activity $$X=(K*A+b)*n$$

in the formula,

X represents an enzyme activity of a sample U/ml, A represents a determined absorbance value of the sample, n represents a dilution multiple of an enzyme solution, K represents a slope of a standard curve, and b represents an intercept of the standard curve.

Figure 2:
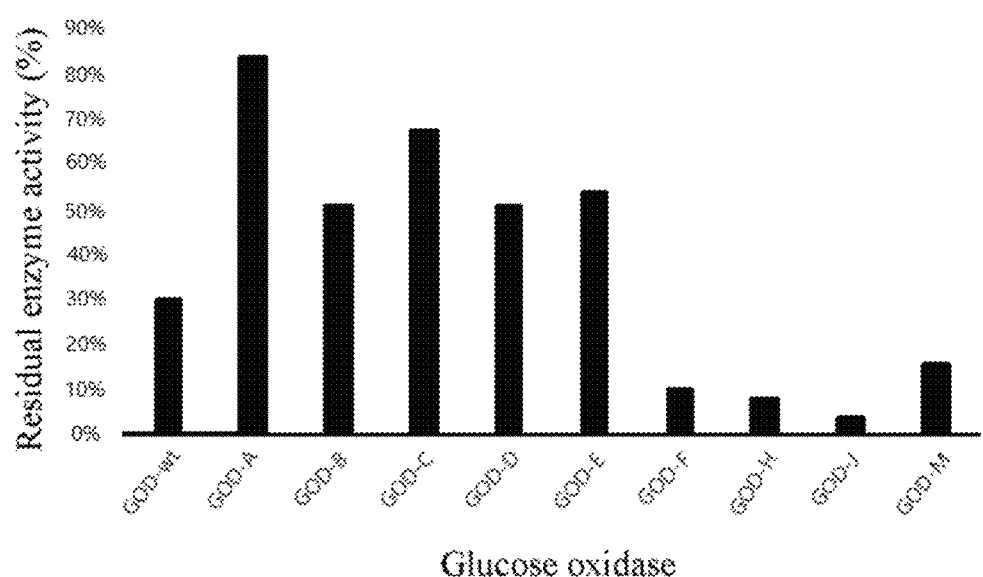
FIG. 2 is a diagram showing determination results of thermal stability of a wild-type glucose oxidase and disulfide bond mutants.

Example 3 Determination of Thermal Stability of Glucose Oxidase and Mutants Thereof The fermentation supernatant obtained in Example 1 was diluted to about 100 U/mL with distilled water and treated at 70° C. for 3 minutes, a residual enzyme activity was determined, and a relative enzyme activity was calculated with an enzyme activity of an untreated sample as 100%. Thermal stability data are shown in FIG. 2 and the table below. The results show that introduction of disulfide bonds has significant influence on the mutants, the introduction of some disulfide bonds such as GOD-G, GOD-I, GOD-K and GOD-L causes that the mutants cannot be expressed normally, such as GOD-G, GOD-I, GOD-K and GOD-L. The introduction of some specific disulfide bonds such as GOD-F, GOD-H, GOD-J and GOD-M causes that the thermal stability of the mutants is lower than that of the wild-type glucose oxidase. In addition, the introduction of other disulfide bonds causes that the thermal stability of the mutants is significantly improved. For example, the thermal stability of GOD-A, GOD-B, GOD-C, GOD-D and GOD-E is significantly improved. Preferably, the residual enzyme activity of the glucose oxidase mutants is improved by 70% or above in comparison with that of the wild-type glucose oxidase. More preferably, the enzyme activity of the glucose oxidase mutants is improved by 120% or above. Particularly preferably, the enzyme activity of the glucose oxidase mutants is improved by 180%. The results above that the mutants with higher thermal stability can be obtained by introducing suitable disulfide bond combinations.

TABLE 3

Results of residual enzyme activity at 70° C.

| Names of mutants | Residual enzyme activity at 70° C. | Improvement in comparison with wild type (%) |
| --- | --- | --- |
| GOD-wt | 30% | / |
| GOD-A | 84% | 180% |
| GOD-B | 51% | 70% |
| GOD-C | 68% | 126% |
| GOD-D | 51% | 70% |
| GOD-E | 54% | 80% |
| GOD-F | 10% | / |
| GOD-H | 8% | / |
| GOD-J | 4% | / |
| GOD-M | 16% | / |

Example 4

As a heat-resistant excellent mutant obtained by mutation screening of a wild-type glucose oxidase (as described in US2016/0068824), F91 has 5 mutants introduced on the basis of a wild type thereof, and a specific sequence is set forth in SEQ ID NO: 8. In order to detect whether or not the disulfide bond mutants described in Example 1 can also achieve functions on the glucose oxidase mutant, and further improve the stability, disulfide bonds A and B were respectively introduced on the basis of a sequence F91 by using the method in Example 1 and named F19-A and F19-B, the two mutants were expressed by using Pichia pastoris and separately incubated at 70° C. and 80° C. for 3 minutes, and then thermal stability was determined by using the method in Example 3. The results are as shown in Table 2 that the thermal stability of the mutants is further improved by introducing the disulfide bonds A and B, improved by 34% and 35% at 70° C. in comparison with that of the mutant F91 respectively, and especially the thermal stability of the mutants at 80° C. is improved. F91 has no residual enzyme activity at 80° C., and residual enzyme activities after addition of the disulfide bonds can reach 12% and 7% respectively, realizing great improvement from zero. It can be seen that as proposed by the inventor, the thermal stability of the glucose oxidase mutant can be more effectively improved by introducing the disulfide bonds.

TABLE 4

Results of residual enzyme activity of F91 before and after introduction of disulfide bonds

| Names of mutants | Residual enzyme activity at 70° C. | Improvement in comparison with the mutant at 70° C. (%) | Residual enzyme activity at 80° C. | Improvement in comparison with the mutant at 80° C. (%) |
|---|---|---|---|---|
| F91 | 70% | / | 0 | / |
| F91-A | 94% | 34% | 12% | — |
| F91-B | 95% | 35% | 7% | — |

Example 5 Determination of Thermal Stability of Glucose Oxidase Mutants Derived from Other *Aspergillus niger* after Introduction of Disulfide Bonds A wild-type glucose oxidase sequence derived from other *Aspergillus niger* is set forth in SEQ ID NO: 9, and has a similarity of 97% with SEQ ID NO: 1. As a heat-resistant excellent mutant obtained by mutation screening of a wild-type glucose oxidase derived from other *Aspergillus niger* (as described in 108893453), GOD-M5 has 5 mutants introduced on the basis of the wild type, and a specific sequence is set forth in SEQ ID NO: 10. In order to detect whether or not the disulfide bond mutants described in Example 1 can also achieve functions on the glucose oxidase mutant derived from other *Aspergillus niger*, and further improve the thermal stability, disulfide bonds A and B were respectively introduced on the basis of a sequence GOD-M5 by using the method in Example 1 and named GOD-M5-A and GOD-M5-B, the two mutants were expressed by using *Pichia pastoris* and separately incubated at 70° C. and 80° C. for 3 minutes, and then thermal stability was determined by using the method in Example 3. The results are as shown in Table 3 that the thermal stability of the mutants is further improved by introducing the disulfide bonds A and B, improved by 350% and 400% especially at 80° C. in comparison with that of the mutant GOD-M5 respectively. It can be seen that as proposed by the inventor, the thermal stability of the glucose oxidase mutant derived from different *Aspergillus niger* can be improved by introducing the disulfide bonds.

TABLE 5

Results of residual enzyme activity of GOD-M5 before and after introduction of disulfide bonds

| Names of mutants | Residual enzyme activity at 70° C. | Improvement in comparison with the mutant at 70° C. (%) | Residual enzyme activity at 80° C. | Improvement in comparison with the mutant at 80° C. (%) |
|---|---|---|---|---|
| GOD-M5 | 94% | / | 4% | / |
| GOD-M5-A | 97.8% | 4% | 18% | 350% |
| GOD-M5-B | 96.3% | 2% | 20% | 400% |

GOD-wt
SEQ ID NO: 1
SNGIEASLLTDPKDVSGRTVDYTTAGGGLTGLTTA

ARLTENPNISVLVIESGSYESDRGPIIEDLNAYGD

IFGSSVDHAYETVELATNNQTALIRSGNGLGGSTL

VNGGTWTRPHKAQVDSWETVFGNEGWNWDNVAAYS

LQAERARAPNAKQIAAGHYFNASCHGVNGTVHAGP

RDTGDDYSPIVKALMSAVEDRGVPTKKDFGCGDPH

GVSMFPNTEHFDQVRSDAAREWLLPNYQRPNLQVL

TGQYVGKVLLSQNGTTPRAVGVEFGTHKGNTIINV

YAKIIEVLLAAGSAVSPTILEYSGIGMKSILEPLG

IDTVVDLPVGLNLQDQTTATVRSRITSAGAGQGQA

AWFATFNETFGDYSEKAHELLNTKLEQWAEEAVAR

GGFHNTTALLIQYENYRDWIVNHNVAYSELFLDTA

GV

GOD-wt
SEQ ID NO: 2
GAATTCAGCAATGGCATTGAAGCCAGCCTCCTGAC

TGATCCCAAGGATGTCTCCGGCCGCACGGTCGACT

ACATCATCGCTGGTGGAGGTCTGACTGGACTCACC

ACCGCTGCTCGTCTGACGGAGAACCCCAACATCAG

TGTGCTCGTCATCGAAAGTGGCTCCTACGAGTCGG

ACAGAGGTCCTATCATTGAGGACCTGAACGCCTAC

GGCGACATCTTTGGCAGCAGTGTAGACCACGCCTA

CGAGACCGTGGAGCTCGCTACCAACAATCAAACCG

CGCTGATCCGCTCCGGAAATGGTCTCGGTGGCTCT

ACTCTAGTGAATGGTGGCACCTGGACTCGCCCCCA

CAAGGCACAGGTTGACTCTTGGGAGACTGTCTTTG

GAAATGAGGGCTGGAACTGGGACAATGTGGCCGCC

TACTCCCTCCAGGCTGAGCGTGCTCGCGCACCAAA

TGCCAAACAGATCGCTGCTGGCCACTACTTCAACG

CATCCTGCCATGGTGTTAATGGTACTGTCCATGCC

GGACCCCGCGACACCGGCGATGACTATTCTCCCAT

CGTCAAGGCTCTCATGAGCGCTGTCGAAGACCGGG

GCGTTCCCACCAAGAAAGACTTCGGATGCGGTGAC

CCCCATGGTGTGTCCATGTTCCCCAACACCTTGCA

CGAAGACCAAGTGCGCTCCGATGCCGCTCGCGAAT

GGCTACTTCCCAACTACCAACGTCCCAACCTGCAA

GTCCTGACCGGACAGTATGTTGGTAAGGTGCTCCT

```
TAGCCAGAACGGCACCACCCCTCGTGCCGTTGGCG

TGGAATTCGGCACCCACAAGGGCAACACCCACAAC

GTTTACGCTAAGCACGAGGTCCTCCTGGCCGCGGG

CTCCGCTGTCTCTCCCACAATCCTCGAATATTCCG

GTATCGGAATGAAGTCCATCCTGGAGCCCCTTGGT

ATCGACACCGTCGTTGACCTGCCCGTCGGCTTGAA

CCTGCAGGACCAGACCACCGCTACCGTCCGCTCCC

GCATCACCTCTGCTGGTGCAGGACAGGGACAGGCC

GCTTGGTTCGCCACCTTCAACGAGACCTTTGGTGA

CTATTCCGAAAAGGCACACGAGCTGCTCAACACCA

AGCTGGAGCAGTGGGCCGAAGAGGCCGTCGCCCGT

GGCGGATTCCACAACACCACCGCCTTGCTCATCCA

GTACGAGAACTACCGCGACTGGATTGTCAACCACA

ACGTCGCGTACTCGGAACTCTTCCTCGACACTGCC

GGAGTAGCCAGCTTCGATGTGTGGGACCTTCTGCC

CTTCACCCGAGGATACGTTCACATCCTCGACAAGG

ACCCCTACCTTCACCACTTCGCCTACGACCCTCAG

TACTTCCTCAACGAGCTGGACCTGCTCGGTCAGGC

TGCCGCTACTCAACTGGCCCGCAACATCTCCAACT

CCGGTGCCATGCAGACCTACTTCGCTGGGGAGACT

ATCCCCGGTGATAACCTCGCGTATGATGCCGATTT

GAGCGCCTGGACTGAGTACATCCCGTACCACTTCC

GTCCTAACTACCATGGCGTGGGTACTTGCTCCATG

ATGCCGAAGGAGATGGGCGGTGTTGTTGATAATGC

TGCCCGTGTGTATGGTGTGCAGGGACTGCGTGTCA

TTGATGGTTCTATTCCTCCTACGCAAATGTCGTCC

CATGTCATGACGGTGTTCTATGCCATGGCGCTAAA

AATTTCGGATGCTATCTTGGAAGATTATGCTTCCA

TGCAGTGAGAGGAAGA
```

GOD-A
SEQ ID NO: 3
```
GAATTCAGCAATGGCATTGAAGCCAGCCTCCTGAC

TGATCCCAAGGATGTCTCCGGCCGCACGGTCGACT

ACATCATCGCTGGTGGAGGTCTGACTGGACTCACC

ACCGCTGCTCGTCTGACGGAGAACCCCAACATCAG

TGTGCTCGTCATCGAAAGTGGCTGCTACGAGTCGG

ACAGAGGTCCTATCATTGAGGACCTGAACGCCTAC

GGCGACATCTTTGGCAGCAGTGTAGACCACGCCTA

CGAGACCGTGGAGCTCGCTACCAACAATCAAACCG

CGCTGATCCGCTCCGGAAATGGTCTCGGTGGCTCT

ACTCTAGTGAATGGTGGCACCTGGACTCGCCCCCA
```

```
CAAGGCACAGGTTGACTCTTGGGAGACTGTCTTTG

GAAATGAGGGCTGGAACTGGGACAATGTGGCCGCC

TACTCCCTCCAGGCTGAGCGTGCTCGCGCACCAAA

TGCCAAACAGATCGCTGCTGGCCACTACTTCAACG

CATCCTGCCATGGTGTTAATGGTACTGTCCATGCC

GGACCCCGCGACACCGGCGATGACTATTCTCCCAT

CGTCAAGGCTCTCATGAGCGCTGTCGAAGACCGGG

GCGTTCCACCAAGAAAGACTTCGGATGCGGTGAC

CCCCATGGTGTGTCCATGTTCCCCAACACCTTGCA

CGAAGACCAAGTGCGCTCCGATGCCGCTCGCGAAT

GGCTACTTCCCAACTACCAACGTCCCAACCTGCAA

GTCCTGTGCGGACAGTATGTTGGTAAGGTGCTCCT

TAGCCAGAACGGCACCACCCCTCGTGCCGTTGGCG

TGGAATTCGGCACCCACAAGGGCAACACCCACAAC

GTTTACGCTAAGCACGAGGTCCTCCTGGCCGCGGG

CTCCGCTGTCTCTCCCACAATCCTCGAATATTCCG

GTATCGGAATGAAGTCCATCCTGGAGCCCCTTGGT

ATCGACACCGTCGTTGACCTGCCCGTCGGCTTGAA

CCTGCAGGACCAGACCACCGCTACCGTCCGCTCCC

GCATCACCTCTGCTGGTGCAGGACAGGGACAGGCC

GCTTGGTTCGCCACCTTCAACGAGACCTTTGGTGA

CTATTCCGAAAAGGCACACGAGCTGCTCAACACCA

AGCTGGAGCAGTGGGCCGAAGAGGCCGTCGCCCGT

GGCGGATTCCACAACACCACCGCCTTGCTCATCCA

GTACGAGAACTACCGCGACTGGATTGTCAACCACA

ACGTCGCGTACTCGGAACTCTTCCTCGACACTGCC

GGAGTAGCCAGCTTCGATGTGTGGGACCTTCTGCC

CTTCACCCGAGGATACGTTCACATCGCGACAAGGA

CCCCTACCTTCACCACTTCGCCTACGACCCTCAGT

ACTTCCTCAACGAGCTGGACCTGCTCGGTCAGGCT

GCCGCTACTCAACTGGCCCGCAACATCTCCAACTC

CGGTGCCATGCAGACCTACTTCGCTGGGGAGACTA

TCCCCGGTGATAACCTCGCGTATGATGCCGATTTG

AGCGCCTGGACTGAGTACATCCCGTACCACTTCCG

TCCTAACTACCATGGCGTGGGTACTTGCTCCATGA

TGCCGAAGGAGATGGGCGGTGTTGTTGATAATGCT

GCCCGTGTGTATGGTGTGCAGGGACTGCGTGTCAT

TGATGGTTCTATTCCTCCTACGCAAATGTCGTCCC

ATGTCATGACGGTGTTCTATGCCATGGCGCTAAAA

ATTTCGGATGCTATCTTGGAAGATTATGCTTCCAT

GCAGTGAGAGGAAGA
```

GOD-B

SEQ ID NO: 4

GAATTCAGCAATGGCATTGAAGCCAGCCTCCTGAC

TGATCCCAAGGATGTCTCCGGCCGCACGGTCGACT

ACATCATCTGCGGTGGAGGTCTGACTGGACTCACC

ACCGCTGCTCGTCTGACGGAGAACCCCAACATCAG

TGTGCTCGTCATCGAAAGTGGCTCCTACGAGTCGG

ACAGAGGTCCTATCATTGAGGACCTGAACGCCTAC

GGCGACATCTTTGGCAGCAGTGTAGACCACGCCTA

CGAGACCGTGGAGCTCGCTACCAACAATCAAACCG

CGCTGATCCGCTCCGGAAATGGTCTCGGTGGCTCT

ACTCTAGTGAATGGTGGCACCTGGACTCGCCCCCA

CAAGGCACAGGTTGACTCTTGGGAGACTGTCTTTG

GAAATGAGGGCTGGAACTGGGACAATGTGGCCGCC

TACTCCCTCCAGGCTGAGCGTGCTCGCGCACCAAA

TGCCAAACAGATCGCTGCTGGCCACTACTTCAACG

CATCCTGCCATGGTGTTAATGGTACTGTCCATGCC

GGACCCCGCGACACCGGCGATGACTATTCTCCCAT

CGTCAAGGCTCTCATGAGCGCTGTCGAAGACCGGG

GCGTTCCCACCAAGAAAGACTTCGGATGCGGTGAC

CCCCATGGTGTGTCCATGTTCCCCAACACCTTGCA

CGAAGACCAAGTGCGCTCCGATGCCGCTCGCGAAT

GGCTACTTCCCAACTACCAACGTCCCAACCTGCAA

GTCCTGACCGGACAGTATTGCGGTAAGGTGCTCCT

TAGCCAGAACGGCACCACCCCTCGTGCCGTTGGCG

TGGAATTCGGCACCCACAAGGGCAACACCCACAAC

GTTTACGCTAAGCACGAGGTCCTCCTGGCCGCGGG

CTCCGCTGTCTCTCCCACAATCCTCGAATATTCCG

GTATCGGAATGAAGTCCATCCTGGAGCCCCTTGGT

ATCGACACCGTCGTTGACCTGCCCGTCGGCTTGAA

CCTGCAGGACCAGACCACCGCTACCGTCCGCTCCC

GCATCACCTCTGCTGGTGCAGGACAGGGACAGGCC

GCTTGGTTCGCCACCTTCAACGAGACCTTTGGTGA

CTATTCCGAAAGGCACACGAGCTGCTCAACACCA

AGCTGGAGCAGTGGGCCGAAGAGGCCGTCGCCCGT

GGCGGATTCCACAACACCACCGCCTTGCTCATCCA

GTACGAGAACTACCGCGACTGGATTGTCAACCACA

ACGTCGCGTACTCGGAACTCTTCCTCGACACTGCC

GGAGTAGCCAGCTTCGATGTGTGGGACCTTCTGCC

CTTCACCCGAGGATACGTTCACATCCTCGACAAGG

ACCCCTACCTTCACCACTTCGCCTACGACCCTCAG

TACTTCCTCAACGAGCTGGACCTGCTCGGTCAGGC

TGCCGCTACTCAACTGGCCCGCAACATCTCCAACT

CCGGTGCCATGCAGACCTACTTCGCTGGGGAGACT

ATCCCCGGTGATAACCTCGCGTATGATGCCGATTT

GAGCGCCTGGACTGAGTACATCCCGTACCACTTCC

GTCCTAACTACCATGGCGTGGGTACTTGCTCCATG

ATGCCGAAGGAGATGGGCGGTGTTGTTGATAATGC

TGCCCGTGTGTATGGTGTGCAGGGACTGCGTGTCA

TTGATGGTTCTATTCCTCCTACGCAAATGTCGTCC

CATGTCATGACGGTGTTCTATGCCATGGCGCTAAA

AATTTCGGATGCTATCTTGGAAGATTATGCTTCCA

TGCAGTGAGAGGAAGA

GOD-C

SEQ ID NO: 5

GAATTCAGCAATGGCATTGAAGCCAGCCTCCTGAC

TGATCCCAAGGATGTCTCCGGCCGCACGGTCGACT

ACATCATCGCTGGTGGAGGTCTGACTGGACTCACC

ACCGCTGCTCGTCTGACGGAGAACCCCAACATCTG

CGTGCTCGTCATCGAAAGTGGCTCCTACGAGTCGG

ACAGAGGTCCTATCATTGAGGACCTGAACGCCTAC

GGCGACATCTTTGGCAGCAGTGTAGACCACGCCTA

CGAGACCGTGGAGCTCGCTACCAACAATCAAACCG

CGCTGATCCGCTCCGGAAATGGTCTCGGTGGCTCT

ACTCTAGTGAATGGTGGCACCTGGACTCGCCCCCA

CAAGGCACAGGTTGACTCTTGGGAGACTGTCTTTG

GAAATGAGGGCTGGAACTGGGACAATGTGGCCGCC

TACTCCCTCCAGGCTGAGCGTGCTCGCGCACCAAA

TGCCAAACAGATCGCTGCTGGCCACTACTTCAACG

CATCCTGCCATGGTGTTAATGGTACTGTCCATGCC

GGACCCCGCGACACCGGCGATGACTATTCTCCCAT

CGTCAAGGCTCTCATGAGCGCTGTCGAAGACCGGG

GCGTTCCCACCAAGAAAGACTTCGGATGCGGTGAC

CCCCATGGTGTGTCCATGTTCCCCAACACCTTGCA

CGAAGACCAAGTGCGCTCCGATGCCGCTCGCGAAT

GGCTACTTCCCAACTACCAACGTCCCAACCTGCAA

GTCCTGACCGGACAGTATGTTGGTAAGGTGCTCCT

TAGCCAGAACGGCACCACCCCTCGTGCCGTTGGCG

TGGAATTCGGCACCCACAAGGGCAACACCCACAAC

GTTTACGCTAAGCACGAGGTCCTCCTGGCCGCGGG

CTCCGCTGTCTCTCCCACAATCCTCGAATATTCCG

GTATCGGAATGAAGTCCATCCTGGAGCCCCTTGGT

ATCGACACCGTCGTTGACCTGCCCGTCGGCTTGAA

-continued

CCTGCAGGACCAGACCACCGCTACCGTCCGCTCCC

GCATCACCTCTGCTGGTGCAGGACAGGGACAGGCC

GCTTGGTTCGCCACCTTCAACGAGACCTTTGGTGA

CTATTCCGAAAAGGCACACGAGCTGCTCAACACCA

AGCTGGAGCAGTGGGCCGAAGAGGCCGTCGCCCGT

GGCGGATTCCACAACACCACCGCCTTGCTCATCCA

GTACGAGAACTACCGCGACTGGATTGTCAACCACA

ACGTCGCGTACTCGGAACTCTTCCTCGACACTGCC

GGAGTAGCCAGCTTCGATGTGTGGGACCTTCTGCC

CTTCACCCGAGGATACGTTCACATCCTCGACAAGG

ACCCCTACCTTCACCACTTCGCCTACGACCCTCAG

TACTTCCTCAACGAGCTGGACCTGCTCGGTCAGGC

TGCCGCTACTCAACTGGCCCGCAACATCTCCAACT

CCGGTGCCATGCAGACCTACTTCGCTGGGGAGACT

ATCCCCGGTGATAACCTCGCGTATGATGCCGATTT

GAGCGCCTGGACTGAGTACATCCCGTACCACTTCC

GTCCTAACTACCATGGCGTGGGTACTTGCTCCATG

ATGCCGAAGGAGATGGGCGGTGTTGTTGATAATGC

TGCCCGTGTGTATGGTGTGCAGGGACTGCGTGTCA

TTGATGGTTCTATTCCTCCTACGCAAATGTCGTCC

CATGTCATGACGGTGTTCTATGCCATGGCGCTAAA

AAATTTCGGATGCTATCTTGGAAGATTATGCTTCC

ATGCAGTGAGAGGAAGA

GOD-D

SEQ ID NO: 6

GAATTCAGCAATGGCATTGAAGCCAGCCTCCTGAC

TGATCCCAAGGATGTCTCCGGCCGCACGGTCGACT

ACATCATCGCTGGTGGAGGTCTGACTGGACTCACC

ACCGCTGCTCGTCTGTGCGAGAACCCCAACATCAG

TGTGCTCGTCATCGAAAGTGGCTCCTACGAGTCGG

ACAGAGGTCCTATCATTGAGGACCTGAACGCCTAC

GGCGACATCTTTGGCAGCAGTGTAGACCACGCCTA

CGAGACCGTGGAGCTCGCTACCAACAATCAAACCG

CGCTGATCCGCTCCGGAAATGGTCTCGGTGGCTCT

ACTCTAGTGAATGGTGGCACCTGGACTCGCCCCCA

CAAGGCACAGGTTGACTCTTGGGAGACTGTCTTTG

GAAATGAGGGCTGGAACTGGGACAATGTGGCCGCC

TACTCCCTCCAGGCTGAGCGTGCTCGCGCACCAAA

TGCCAAACAGATCGCTGCTGGCCACTACTTCAACG

CATCCTGCCATGGTGTTAATGGTACTGTCCATGCC

GGACCCCGCGACACCGGCGATGACTATTCTCCCAT

-continued

CGTCAAGGCTCTCATGAGCGCTGTCGAAGACCGGG

GCGTTCCCACCAAGAAAGACTTCGGATGCGGTGAC

CCCCATGGTGTGTCCATGTTCCCCAACACCTTGCA

CGAAGACCAAGTGCGCTCCGATGCCGCTCGCGAAT

GGCTACTTCCCAACTACCAACGTCCCAACTGCCAA

GTCCTGACCGGACAGTATGTTGGTAAGGTGCTCCT

TAGCCAGAACGGCACCACCCCTCGTGCCGTTGGCG

TGGAATTCGGCACCCACAAGGGCAACACCCACAAC

GTTTACGCTAAGCACGAGGTCCTCCTGGCCGCGGG

CTCCGCTGTCTCTCCCACAATCCTCGAATATTCCG

GTATCGGAATGAAGTCCATCCTGGAGCCCCTTGGT

ATCGACACCGTCGTTGACCTGCCCGTCGGCTTGAA

CCTGCAGGACCAGACCACCGCTACCGTCCGCTCCC

GCATCACCTCTGCTGGTGCAGGACAGGGACAGGCC

GCTTGGTTCGCCACCTTCAACGAGACCTTTGGTGA

CTATTCCGAAAAGGCACACGAGCTGCTCAACACCA

AGCTGGAGCAGTGGGCCGAAGAGGCCGTCGCCCGT

GGCGGATTCCACAACACCACCGCCTTGCTCATCCA

GTACGAGAACTACCGCGACTGGATTGTCAACCACA

ACGTCGCGTACTCGGAACTCTTCCTCGACACTGCC

GGAGTAGCCAGCTTCGATGTGTGGGACCTTCTGCC

CTTCACCCGAGGATACGTTCACATCCTCGACAAGG

ACCCCTACCTTCACCACTTCGCCTACGACCCTCAG

TACTTCCTCAACGAGCTGGACCTGCTCGGTCAGGC

TGCCGCTACTCAACTGGCCCGCAACATCTCCAACT

CCGGTGCCATGCAGACCTACTTCGCTGGGGAGACT

ATCCCCGGTGATAACCTCGCGTATGATGCCGATTT

GAGCGCCTGGACTGAGTACATCCCGTACCACTTCC

GTCCTAACTACCATGGCGTGGGTACTTGCTCCATG

ATGCCGAAGGAGATGGGCGGTGTTGTTGATAATGC

TGCCCGTGTGTATGGTGTGCAGGGACTGCGTGTCA

TTGATGGTTCTATTCCTCCTACGCAAATGTCGTCC

CATGTCATGACGGTGTTCTATGCCATGGCGCTAAA

AATTTCGGATGCTATCTTGGAAGATTATGCTTCCA

TGCAGTGAGAGGAAGA

GOD-E

SEQ ID NO: 7

GAATTCAGCAATGGCATTGAAGCCAGCCTCCTGAC

TGATCCCAAGGATGTCTCCGGCCGCACGGTCGACT

ACATCATCGCTGGTGGAGGTCTGACTGGACTCACC

ACCGCTGCTCGTCTGACGGAGAACCCCAACATCAG

TGTGCTCGTCATCGAAAGTGGCTCCTACGAGTCGG

ACAGAGGTCCTATCATTGAGGACCTGAACGCCTAC
GGCGACATCTTTGGCAGCAGTGTAGACCACGCCTA
CGAGACCGTGGAGCTCGCTTGCAACAATCAAACCG
CGCTGATCCGCTCCGGAAATGGTCTCGGTGGCTCT
ACTCTAGTGAATGGTGGCACGGGACTCGCCCCCAC
AAGGCACAGGTTGACTCTTGGGAGACTGTCTTTGG
AAATGAGGGCTGGAACTGGGACAATGTGGCCGCCT
ACTCCCTCCAGGCTGAGCGTGCTCGCGCACCAAAT
GCCAAACAGATCGCTGCTGGCCACTACTTCAACGC
ATCCTGCCATGGTGTTAATGGTACTGTCCATGCCG
GACCCCGCGACACCGGCGATGACTATTCTCCCATC
GTCAAGGCTCTCATGAGCGCTGTCGAAGACCGGGG
CGTTCCCACCAAGAAAGACTTCGGATGCGGTGACC
CCCATGGTGTGTCCATGTTCCCCAACACCTTGCAC
GAAGACCAAGTGCGCTCCGATGCCGCTCGCGAATG
GCTACTTCCCAACTACCAACGTCCCAACCTGCAAG
TCCTGACCGGACAGTATGTTGGTAAGGTGCTCCTT
AGCCAGAACGGCACCACCCCTCGTGCCGTTGGCGT
GGAATTCGGCACCCACAAGGGCAACACCCACAACG
TTTACGCTAAGCACGAGGTCCTCCTGGCCGCGGGC
TCCGCTGTCTCTCCCACAATCCTCGAATATTCCGG
TATCGGAATGAAGTCCATCCTGGAGCCCCTTGGTA
TCGACACCGTCGTTGACCTGCCCGTCGGCTTGAAC
CTGCAGGACCAGACCACCGCTACCGTCCGCTCCCG
CATCACCTCTGCTGGTGCAGGACAGGGACAGGCCG
CTTGGTTCGCCACCTTCAACGAGACCTTTGGTGAC
TATTCCGAAAAGGCACACGAGCTGCTCAACACCAA
GCTGGAGCAGTGGGCCGAAGAGGCCGTCGCCCGTG
GCGGATTCCACAACACCACCGCCTTGCTCATCCAG
TACGAGAACTACCGCGACTGGATTGTCAACCACAA
CGTCGCGTACTCGGAACTCTTCCTCGACACTGCCG
GAGTAGCCAGCTTCGATGTGTGGGACCTTCTGCCC
TTCACCCGAGGATACGTTCACATCCTCGACAAGGA
CCCCTACCTTCACCACTTCGCCTACGACCCTCAGT
ACTTCCTCAACGAGCTGGACCTGCTCGGTCAGGCT
GCCGCTACTCAACTGGCCCGCAACATCTCCAACTC
CGGTGCCATGCAGACCTACTTCGCTGGGGAGACTA
TCCCCGGTGATAACCTCGCGTATGATGCCGATTTG
AGCGCCTGGACTGAGTACATCTGCTACCACTTCCG
TCCTAACTACCATGGCGTGGGTACTTGCTCCATGA

TGCCGAAGGAGATGGGCGGTGTTGTTGATAATGCT
GCCCGTGTGTATGGTGTGCAGGGACTGCGTGTCAT
TGATGGTTCTATTCCTCCTACGCAAATGTCGTCCC
ATGTCATGACGGTGTTCTATGCCATGGCGCTAAAA
ATTTCGGATGCTATCTTGGAAGATTATGCTTCCAT
GCAGTGAGAGGAAGA

F19
SEQ ID NO: 8
SNGIEASLLTDPKDVSGRTVDYIIAGGGLVGLTTA
AKLTENPNISVLVIESGSYESDRGPIIEDLNAYGD
IFGSSVDHAYETVELATNNQTALVRSGNLGGSTI
INGGTWTRPHKAQVDSWETVFGNEGWNWDNVAAYS
LQAERARAPNAKQIAAGHYFNTSCHGVNGTVHAGP
RDTGDDYSPIVKALMSAVEDRGVPIKKDFGCGDPH
GVSMFPNTLHEDQVRSDAAREWLLPNYQRPNLQVL
TGQYVGKVLLSQNGTTPRAVGVEFGTHKGNTHNVY
AKHEVLLAAGSAVSPTILEYSGIGMKSILEPLGID
TVVDLPVGLNLQDQTTATVRSRITSAGAGQGQAAW
FATFNETFGDYSEKAHELLNTKLEQWAEEAVARGG
FHNTTALLIQYENYRDWIVNHNVAYSELFLDTAGV
ASFDVWDLLPFTRGYVHILDKDPYLEHFAYDPQYF
LNELDLLGQAAATQLARNISNSGAMQTYFAGETIP
GDNLAYDADLSAWTEYIPYHFRPNYHGVGTCSMMP
KEIVIGGVVDNAARVYGVQGLRVIDGSIPPTQMSS
HVMTVFYAMALKISDAILEDYASMQ

SEQ ID NO: 9
SNGIEASLLTDPKEVAGRTVDYIIAGGGLIGLITA
ARLTENPDITVLVIESGSYESDRGPIIEDLNAYGD
IFGSSVDHAYETVELATNNQTALIRSGNLGGSTL
VNGGTWTRPHKAQVDSWETVFGNEGWNWDSVAAYS
LQAERARAPNAKQIAAGHYFNASCHGINGTVHAGP
RDTGDDYSPIVKALMSAVEDRGVPIKKDLGCGDPH
GVSMFPNTLEIEDQVRSDAAREWLLPNYQRPNLQV
LTGQYVGKVLLSQNATTPRAVGVEFGTHKGNTHNV
YAKHEVLLAAGSAVSPTILEYSGIGMKSILEPLGI
DTVVDLPVGLNLQDQTTSTVRSRITSAGAGQGQAA
WFATFNETFGDYTEKAHELLNTKLEQWAEEAVARG
GFHNTTALLIQYENYRDWIVKDNVAYSELFLDTAG
VASFDVWDLLPFTRGYVHILDKDPYLRHFAYDPQY
FLNELDLLGQAAATQLARNISNSGAMQTYFAGETI
PGDNLAYDADLRAWVEYIPYNFRPNYHGVGTCSMI

-continued

MPKEMGGVVDNAARVYGVQGLRVIDGSIPPTQMSS

HVMTVFYAMALKIADAVLADYASMQ

GOD-M5

SEQ ID NO: 10

SNGIEASLLTDPKEVAGRTVDYIIAGGGLTGLTVA

ARLTENPDITVLVIESGSYESDRGPIIEDLNAYGD

WGSSVDHAYETVCLATNNQTALIRSGNGLGGSTLV

NGGTWTRPHKAQVDSWETVFGNEGWNWDSVAAYSL

QAERARAPNAKQIAAGHYFNASCHGINGTVHAGPR

DTGDDYSPIVKALMSAVEDRGVPIKKDLGCGDPHG

VSMFPNTLHEDQVRSDAAREWLLPNYQRPNLQVLT

GQYVGKVLLSQNATTPRAVGVEFGTHKGNTHNVYA

KHEVLLAAGSAVSPTILEYSGIGMKSTLEPLGIKT

VVDLPVGLNLQDQTTSTVRSRITSAGAGQGQAAWF

ATFNETFGDYTEKAHELLNTKLEQWAEEAVARGGF

HNTTALLIQYENYRDWIVKDNVAYSELFLDTAGEA

SFDVWDLLPFTRGYVHILDKDPYLRHFAYDPQYFL

NELDLLGQAAATQLARNISNSGAMQTYFAGETIPG

DNLAYDADLRAWVEYIPYHFRPNYHGVGTCSMMPK

EMGGVVDNAARVYGVQGLRVIDGSIPPTQMSSHVM

TVFYAMALKIADAVLADYASMQ

GOD-A

SEQ ID NO: 11

SNGIEASLLTDPKDVSGRTVDYIIAGGGLTGLTTA

ARLTENPNISVLVIESGCYESDRGPIIEDLNAYGD

IFGSSVDHAYETVELATNNQTALIRSGNGLGGSTL

VNGGTWTRPHKAQVDSWETVFGNEGWNWDNVAAYS

LQAERARAPNAKQIAAGHYFNASCHGVNGTVHAGP

RDTGDDYSPIVKALMSAVEDRGVPTKKDFGCGDPH

GVSMFPNTLHEDQVRSDAAREWLLPNYQRPNLQVL

CGQYVGKVLLSQNGTTPRAVGVEFGTHKGNTHNVY

AKHEVLLAAGSAVSPTILEYSGIGMKSILEPLGID

TVVDLPVGLNLQDQTTATVRSRITSAGAGQGQAAW

FATFNETFGDYSEKAHELLNTKLEQWAEEAVARGG

FHNTTALLIQYENYRDWIVNHNVAYSELFLDTAGV

ASFDVWDLLPFTRGYVHILDKDPYLHHFAYDPQYF

LNELDLLGQAAATQLARNISNSGAMQTYFAGETIP

GDNLAYDADLSAWTEYIPYHFRPNYHGVGICSMIM

PKEMGGVVDNAARVYGVQGLRVIDGSIPPTQMSSH

VMTVFYAMALKISDAILEDYASMQ

GOD-B

SEQ ID NO: 12

SNGILASLLTDPKDVSGRTVDYIICGGGLTGLTTA

ARLTENPNISVLVIESGSYESDRGPIIEDLNAYGD

WGSSVDHAYETVELATNNQTALIRSGNGLGGSTLV

NGGTWTRPHKAQVDSWETVFGNEGWNWDNVAAYSL

QAERARAPNAKQIAAGHYFNASCHGVNGTVHAGPR

DTGDDYSPIVKALMSAVEDRGVPTKKDFGCGDPHG

VSNIFPNTLHEDQVRSDAAREWLLPNYQRPNLQVL

TGQYCGKVLLSQNGTTPRAVGVEFGTHKGNTHNVY

AKHEVLLAAGSAVSPTILEYSGIGMKSILEPLGID

TVVDLPVGLNLQDQTTATVRSRITSAGAGQGQAAW

FATFNETFGDYSEKAHELLNTKLEQWAEEAVARGG

FHNTTALLIQYENYRDWIVNHNVAYSFLFLDTAGV

ASFDVWDLLPFTRGYVHILDKDPYLHHFAYDPQYF

LNELDLLGQAAATQLARNISNSGAMQTYFAG

ETIPGDNLAYDADLSAWTEYIPYHFRPNYHGVGTC

SMMPKEMGGVVDNAARVYGVQGLRVIDGSIPPTQM

SSHVMTVFYAMALKISDAILEDYASMQ

GOD-C

SEQ ID NO: 13

SNGIEASLLTDPKDVSGRTCDYIIAGGGLTGLTTA

ARLIENPNICVLVIESGSYESDRGPIIEDLNAYGD

WGSSVDHAYETVELATNNQTALIRSGNGLGGSTLV

NGGTWTRPHKAQVDSWETVFGNEGWNWDNVAAYSL

QAERARAPNAKQIAAGHYFNASCHGVNGTVHAGPR

DTGDDYSPIVKALMSAVEDRGVPTKKDFGCGDPHG

VSNIFPNTLHEDQVRSDAAREWLLPNYQRPNLQVL

TGQYVGKVLLSQNGTTPRAVGVEFGTHKGNTHNVY

AKHEVLLAAGSAVSPTILEYSGIGMKSILEPLGID

TVVDLPVGLNLQDQTTATVRSRITSAGAGQGQAAW

FATFNETFGDYSEKAHELLNTKLEQWAEEAVARGG

FHNTTALLIQYENYRDWIVNHNVAYSELFLDTAGV

ASFDVWDLLPFTRGYVHILDKDPYLHIWAYDPQYF

LNELDLLGQAAATQLARNISNSGAMQTYFAGETIP

GDNLAYDADLSAWTEYIPYHFRPNYHGVGTCSMIM

PKEMGGVVDNAARVYGVQGLRVIDGSIPPTQMSSH

VMTVFYAMALKISDAILEDYASMQ

GOD-D

SEQ ID NO: 14

SNGIEASLLTDPKDVSGRTVDYIIAGGGLTGLTTA

ARLCENPNISVLVIESGSYESDRGPIIEDLNAYGD

IFGSSVDHAYETVELATNNQTALIRSGNGLGGSTL

VNGGTWTRPHKAQVDSWETVFGNEGWNWDNVAAYS
LQAERARAPNAKQIAAGHYFNASCHGVNGTVHAGP
RDTGDDYSPIVKALMSAVEDRGVPTKKDFGCGDPH
GVSMFPNTLHEDQVRSDAAREWLLPNYQRPNCQVL
TGQYVGKVLLSQNGTTPRAVGVEFGTHKGNTHNVY
AKHEVLLAAGSAVSPTILEYSGIGMKSILEPLGID
TVVDLPVGLNLQDQTTATVRSRITSAGAGQGQAAW
FATFNETFGDYSEKAHELLNTKLEQWAEEAVARGG
FHNTTALLIQYENYRDWIVNHNVAYSELFLDTAGV
ASFDVWDLLPFTRGYVHILDKDPYLITHFAYDPQY
FLNELDLLGQAAATQLARNISNSGAMQTYFAGETI
PGDNLAYDADLSAWTEYIPYHFRPNYHGVGTCSMM
PKEMGGVVDNAARVYGVQGLRVIDGSIPPTQMSSH
VMTVFYAMALKISDAILEDYASMQ
GOD-E
SEQ ID NO: 15
SNGIEASLLTDPKDVSGRTVDYIIAGGGLTGLTTA
ARLTENPNISVLVIESGSYESDRGPIIEDLNAYGD
IFGSSVDHAYETVELACNNQTALIRSGNGLGGSTL
VNGGIWTRPIIKAQVDSWETVFGNEGWNWDNVAAY
SLQAERARAPNAKQIAAGHYFNASCHGVNGTVHAG
PRDTGDDYSPIVKALMSAVEDRGVPTKKDFGCGDP
HGVSMFPNTLHEDQVRSDAAREWLLPNYQRPNLQV
LTGQYVGKVLLSQNGTTPRAVGVEFGTHKGNTHNV
YAKHEVLLAAGSAVSPTILEYSGIGMKSILEPLGI
DTVVDLPVGLNLQDQTTATVRSRITSAGAGQGQAA
WFATFNETFGDYSEKAHELLNTKLEQWAEEAVARG
GFHNTTALLIQYENYRDWIVNHNVAYSELFLDTAG
VASFDVWDLLPFTRGYVHILDKOPYLFITIFAYDP
QYFLNELDLLGQAAATQLARNISNSGAMQTYFAGE
TIPGDNLAYDADLSAWTEYICYHFRPNYHGVGTCS
MMPKEMGGVVDNAARVYGVQGLRVIDGSIPPTQMS
SHVMTVFYAMALKISDAILEDYASMQ

F19-A
SEQ ID NO: 16
GAATTCAGCAATGGCATTGAAGCCAGCCTCCTGAC
TGATCCCAAGGATGMTCCGGCCGCACGGTCGACTA
CATCATCGCTGGTGGAGGTCTGGTGGGACTCACCA
CCGCTGCTAAGCTGACGGAGAACCCCAACATCAGT
GTGCTCGTCATCGAAAGTGGCTGCTACGAGTCGGA
CAGAGGTCGATCATTGAGGACCTGAACGCCTACGG
CGACATCTTTGGCAGCAGTGTAGACCACGCCTACG
AGACCGTGGAGCTCGCTACCAACAATCAAACCGCG

CTGGTGCGCTCCGGAAATGGTCTCGGTGGCTCTAC
TCTAATCAATGGTGGCACCTGGACTCGCCCCCACA
AGGCACAGGTTGACTCTTGGGAGACTGTCTTTGGA
AATGAGGGCTGGAACTGGGACAATGTGGCCGCCTA
CTCCCTCCAGGCTGAGCGTGCTCGCGCACCAAATG
CCAAACAGATCGCTGCTGGCCACTACTTCAACACC
TCCTGCCATGGTGTTAATGGTACTGTCCATGCCGG
ACCCCGCGACACCGGCGATGACTATTCTCCCATCG
TCAAGGCTCTCATGAGCGCTGTCGAAGACCGGGGC
GTTCCCACCAAGAAAGACTTCGGATGCGGTGACCC
CCATGGTGTGTCCATGTTCCCCAACACCTTGCACG
AAGACCAAGTGCGCTCCGATGCCGCTCGCGAATGG
CTACTTCCCAACTACCAACGTCCCAACCTGCAAGT
CCTGTGCGGACAGTATGTTGGTAAGGTGCTCCTTA
GCCAGAACGGCACCACCCCTCGTGCCGTTGGCGTG
GAATTCGGCACCCACAAGGGCAACACCCACAACGT
TTACGCTAAGCACGAGGTCCTCCTGGCCGCGGGCT
CCGCTGTCTCTCCCACAATCCTCGAATATTCCGGT
ATCGGAATGAAGTCCATCCTGGAGCCCCTTGGTAT
CGACACCGTCGTTGACCTGCCCGTCGGCTTGAACC
TGCAGGACCAGACCACCGCTACCGTCCGCTCCCGC
ATCACCTCTGCTGGTGCAGGACAGGGACAGGCCGC
TTGGTTCGCCACCTTCAACGAGACCTTTGGTGACT
ATTCCGAAAAGGCACACGAGCTGCTCAACACCAAG
CTGGAGCAGTGGGCCGAAGAGGCCGTCGCCCGTGG
CGGATTCCACAACACCACCGCCTTGCTCATCCAGT
ACGAGAACTACCGCGACTGGATTGTCAACCACAAC
GTCGCGTACTCGGAACTCTTCCTCGACACTGCCGG
AGTAGCCAGCTTCGATGTGTGGGACCTTCTGCCCT
TCACCCGAGGATACGTTCACATCCTCGACAAGGAC
CCCTACCTTACCCACTTCGCCTACGACCCTCAGTA
CTTCCTCAACGAGCTGGACCTGCTCGGTCAGGCTG
CCGCTACTCAACTGGCCCGCAACATCTCCAACTCC
GGTGCCATGCAGACCTACTTCGCTGGGGAGACTAT
CCCCGGTGATAACCTCGCGTATGATGCCGATTTGA
GCGCCTGGACTGAGTACATCCCGTACCACTTCCGT
CCTAACTACCATGGCGTGGGTACTTGCTCCATGAT
GCCGAAGGAGATGGGCGGTGTTGTTGATAATGCTG
CCCGTGTGTATGGTGTGCAGGGACTGCGTGTCATT
GATGGTTCTATTCCTCCTACGCAAATGTCGTCCCA

```
TGTCATGACGGTGTTCTATGCCATGGCGCTAAAAA
TTTCGGATGCTATCTTGGAAGATTATGCTTCCATG
CAGTGAGAGGAAGA
```

F19-A

SEQ ID NO: 17
```
SNGIEASLLTDPKDVSGRTVDYIIAGGGLVGLTTA
AKLTENPNISVLVIESGCYESDRGPIIEDLNAYGD
IFGSSVDHAYETVELATNNQTALVRSGNGLGGSTL
INGGTWTRPHKAQVDSWETVFGNEGWNWDNVAAYS
LQAERARAPNAKQIAAGHYFNTSCHGVNGTVHAGP
RDTGDDYSPIVKALMSAVEDRGVPTKKDFCCGDPH
GVSMFPNTLHEDQVRSDAAREWLLPNYQRPNLQVL
CGQYVGKVLLSQNGTTPRAVGVEFGTHKGNTHNVY
AKHEVLLAAGSAVSPTILEYSGIGMKSILEPLGID
TVVDLPVGLNLQDQTTATVRSRITSAGAGQGQAAW
FATFNETFGDYSEKAHELLNTKLEQWAEEAVARGG
FHNTTALLIQYENYRDWIVNHNVAYSELFLDTAGV
ASFDVWDLLPFTRGYVHILDKDPYLEHFAYDPQYF
LNELDLLGQAAATQLARNISNSGAMQTYFAGETIP
GDNLAYDADLSAWTEYWYHFRPNYHGVGTCSMMPK
EMGGVVDNAARVYGVQGLRVIDGSIPPTQMSSHVM
TVFYAMALKISDAILEDYASMQ
```

F19-B

SEQ ID NO: 18
```
GAATTCAGCAATGGCATTGAAGCCAGCCTCCTGAC
TGATCCCAAGGATGICTCCGGCCGCACGGTCGACT
ACATCATCTGCGGTGGAGGTCTGGTGGGACTCACC
ACCGCTGCTAAGCTGACGGAGAACCCCAACATCAG
TGTGCTCGTCATCGAAAGTGGCTCCTACGAGTCGG
ACAGAGGTCCTATCATTGAGGACCTGAACGCCTAC
GGCGACATCTTTGGCAGCAGTGTAGACCACGCCTA
CGAGACCGTGGAGCTCGCTACCAACAATCAAACCG
CGCTGGTGCGCTCCGGAAATGGTCTCGGTGGCTCT
ACTCTAATCAATGGTGGCACCTGGACTCGCCCCCA
CAAGGCACAGGTTGACTCTTGGGAGACTGTCTTTG
GAAATGAGGGCTGGAACTGGGACAATGTGGCCGCC
TACTCCCTCCAGGCTGAGCGTGCTCGCGCACCAAA
TGCCAAACAGATCGCTGCTGGCCACTACTTCAACA
CCTCCTGCCATGGTGTTAATGGTACTGTCCATGCC
GGACCCCGCGACACCGGCGATGACTATTCTCCCAT
CGTCAAGGCTCTCATGAGCGCTGTCGAAGACCGGG
GCGTTCCACCAAGAAAGACTTCGGATGCGGTGAC
CCCCATGGTGTGTCCATGTTCCCCAACACCTTGCA
```

F19-B

```
CGAAGACCAAGTGCGCTCCGATGCCGCTCGCGAAT
GGCTACTTCCCAACTACCAACGTCCCAACCTGCAA
GTCCTGACCGGACAGTATTGCGGTAAGGTGCTCCT
TAGCCAGAACGGCACCACCCCTCGTGCCGTTGGCG
TGGAATTCGGCACCCACAAGGGCAACACCCACAAC
GTTTACGCTAAGCACGAGGICCTCCTGGCCGCGGG
CTCCGCTGTCTCTCCCACAATCCTCGAATATTCCG
GTATCGGAATGAAGTCCATCCTGGAGCCCCTTGGT
ATCGACACCGTCGTTGACCTGCCCGTCGGCTTGAA
CCTGCAGGACCAGACCACCGCTACCGTCCGCTCCC
GCATCACCTCTGCTGGTGCAGGACAGGGACAGGCC
GCTTGGTTCGCCACCTTCAACGAGACCTTTGGTGA
CTATTCCGAAAAGGCACACGAGCTGCTCAACACCA
AGCTGGAGCAGTGGGCCGAAGAGGCCGTCGCCCGT
GGCGGATTCCACAACACCACCGCCTTGCTCATCCA
GTACGAGAACTACCGCGACTGGATTGTCAACCACA
ACGTCGCGTACTCGGAACTCTTCCTCGACACTGCC
GGAGTAGCCAGCTTCGATGTGTGGGACCTTCTGCC
CTTCACCCGAGGATACGTTCACATCCTCGACAAGG
ACCCCTACCTTCACCACTTCGCCTACGACCCTCAG
TACTTCCTCAACGAGCTGGACCTGCTCGGTCAGGC
TGCCGCTACTCAACTGGCCCGCAACATCTCCAACT
CCGGTGCCATGCAGACCTACTTCGCTGGGGAGACT
ATCCCCGGTGATAACCTCGCGTATGATGCCGATTT
GAGCGCCTGGACTGAGTACATCCCGTACCACTTCC
GTCCTAACTACCATGGCGTGGGTACTTGCTCCATG
ATGCCGAAGGAGATGGGCGGTGTTGTTGATAATGC
TGCCCGTGTGTATGGTGTGCAGGGACTGCGTGTCA
TTGATGGTTCTATTCCTCCTACGCAAATGTCGTCC
CATGTCATGACGGTGTTCTATGCCATGGCGCTAAA
AATTTCGGATGCTATCTTGGAAGATTATGCTTCCA
TGCAGTGAGAGGAAGA
```

F19-B

SEQ ID NO: 19
```
SNGIEASLLTDPKDVSGRTVDYIICGGGLVGLTTA
AKLTENPNISVLVIESGSYESDRGPIIEDLNAYGD
IFGSSVDHAYETVELATNNQTALVRSGNGLGGSTL
INGGTWTRPHKAQVDSWETVFGNEGWNWDNVAAYS
LQAERARAPNAKQIAAGHYFNTSCHGVNGTVHAGP
RDTGDDYSPIVKALMSAVEDRGVPTKKDFGCGDPH
GVSMFPNTLHEDQVRSDAAREWLLPNYQRPNLQVL
```

-continued

TGQYCGKVLLSQNGTTPRAVGVEFGTHKGNTHNVY

AKHEVLLAAGSAVSPTILEYSGIGMKSILEPLGID

TVVDLPVGLNLQDQTTATVRSRITSAGAGQGQAAW

FATFNETFGDYSEKAIIELLNTKLEQWAEEAVARG

GFHNTTALLIQYENYRDWIVNHNVAYSELFLDTAG

VASFDVWDLLPFTRGYVHILDKDPYLHHFAYDPQY

FLNELDLLGQAAATQLARNISNSGAMQTYFAGETI

PGDNLAYDADLSAWIEYWYHFRPNYHGVGTCSMMP

KEMGGVVDNAARVYGVQGLRVIDGSIPPTQMSSHV

MTVFYAMALKISDAILEDYASMQ

GOD-M5-A

SEQ ID NO: 20

GAATTCAGCAATGGAATTGAAGCAAGCCTCCTGAC

TGACCCCAAGGAGGTTGCCGGCCGCACTGTCGACT

ACATCATCGCTGGTGGAGGTCTGACTGGACTCACC

GTCGCTGCCCGTCTGACGGAGAACCCCGATATCAC

TGTGCTTGTCATCGAAAGTGGCTGCTACGAGTCTG

ACAGAGGTCCTATCATTGAGGACCTGAACGCTTAC

GGTGACATTTTTGGCAGCAGTGTGGACCACGCCTA

CGAGACTGTCTGCCTCGCCACCAACAATCAGACTG

CGCTGATCCGCTCCGGAAATGGTCTCGGTGGCTCT

ACCCTCGTCAACGGTGGCACCTGGACTCGCCCCCA

CAAGGCACAAGTTGACTCATGGGAGACCGTCTTCG

GAAATGAGGGCTGGAACTGGGACAGCGTGGCCGCC

TACTCCCTCCAGGCTGAGCGTGCTCGCGCACCAAA

TGCCAAACAGATTGCTGCTGGCCACTACTTTAATG

CATCCTGCCATGGTATCAATGGTACTGTCCACGCC

GGACCCCGCGATACCGGTGATGACTACTCCCCCAT

CGTCAAGGCTCTCATGAGCGCTGTCGAAGACAGGG

GCGTTCCACCAAGAAGGACTTGGGATGCGGTGAC

CCCCATGGTGTGTCCATGTTCCCCAACACCTTGCA

CGAAGACCAAGTGCGCTCTGATGCCGCTCGCGAAT

GGCTCCTCCCCAACTACCAGCGTCCCAACCTGCAA

GTCCTCTGCGGACAGTATGTTGGAAAGGTCCTGCT

CAGCCAGAACGCTACCACACCTCGTGCCGTTGGCG

TGGAATTCGGCACCCACAAGGGCAACACCCACAAC

GTCTACGCTAAGCACGAGGTCCTCCTGGCCGCTGG

ATCCGCTGTCTCTCCCACCATCCTCGAATATTCCG

GTATCGGAATGAAGTCCATTCTAGAGCCTCTTGGA

ATTAAGACCGTCGTTGACCTGCCCGTTGGTCTCAA

-continued

CCTTCAGGACCAGACCACCTCTACCGTCCGCTCAC

GCATTACCTCCGCCGGTGCCGGACAGGGACAGGCC

GCTTGGTTCGCTACCTTCAACGAGACCTTTGGCGA

CTACACCGAAAAGGCTCACGAGCTGCTCAACACCA

AGCTGGAGCAGTGGGCCGAAGAGGCCGTCGCCCGT

GGCGGATTCCACAACACCACCGCTTTGCTCATCCA

GTACGAGAACTACCGCGACTGGATCGTCAAGGACA

ATGTCGCATACTCGGAACTCTTCCTCGACACGGCC

GGAGAAGCCAGTTTCGATGTGTGGGATCTTCTGCC

CTTCACTAGAGGATACGTCCACATCCTCGACAAGG

ACCCCTACCTCCGCCATTTCGCCTACGACCCTCAG

TACTTCCTCAACGAGCTTGACCTGCTCGGCCAGGC

TGCCGCCACTCAGCTGGCCCGCAACATCTCTAACT

CCGGTGCCATGCAAACTTATTTCGCTGGAGAGACT

ATTCCCGGTGACAACCTCGCGTATGATGCCGACTT

GAGAGCCTGGGTTGAGTATATCCCGTACCACTTCC

GCCCTAACTACCATGGTGTGGGTACTTGCTCCATG

ATGCCGAAGGAGATGGGCGGTGTTGTCGACAATGC

TGCCCGTGTGTATGGTGTGCAGGGACTGCGAGTCA

TCGATGGTTCTATTCCCCCTACGCAGATGTCGTCC

CATGTTATGACGGTCTTTTATGCCATGGCCTTAAA

GATTGCGGATGCCGTCTTGGCGGATTACGCTTCTA

TGCAGTAAGAGGAAGA

GOD-M5-A

SEQ ID NO: 21

SNGIEASLLTDPKEVAGRTVDYIIAGGGLTGLTVA

ARLTENPDITVLVIESGCYESDRGPIIEDLNAYGD

IFGSSVDHAYETVCLATNNQTALIRSGNGLGGSTL

VNGGTWTRPHKAQVDSWETVFGNEGWNWDSVAAYS

LQAERARAPNAKQIAAGHYFNASCHUNGTVHAGPR

DTGDDYSPIVKALMSAVEDRGVPTKKDLGCGDPHG

VSMFPNTLHEDQVRSDAAREWLLPNYQRPNLQVLC

GQYVGKVLLSQNATTPRAVGVEFGTHKGNTHNVYA

KHEVLLAAGSAVSPTILEYSGIGMKSILEPLGIKT

VVDLPVGLNLQDQTTSTVRSRITSAGAGQGQAAWF

ATFNETFGDYTEKAHELLNTKLEQWAEEAVARGGF

HNTTALLIQYENYRDWIVKDNVAYSELFLDTAGEA

SFDVWDLLPFTRGYVHILDKDPYLRHFAYDPQYFL

NELDLLGQAAATQLARNISNSGAMQTYFAGETIPG

DNLAYDADLRAWVEYIPYHFRPNYHGVGTCSMMPK

EMGGVVDNAARVYGVQGLRVIDGSIPPTQMSSHVM

TVFYAMALKIADAVLADYASMQ

GOD-M5-B

SEQ ID NO: 22

GAATTCAGCAATGGAATTGAAGCAAGCCTCCTGAC

TGACCCCAAGGAGGTTGCCGGCCGCACTGTCGACT

ACATCATCTGCGGTGGAGGTCTGACTGGACTCACC

GTCGCTGCCCGTCTGACGGAGAACCCCGATATCAC

TGTGCTTGTCATCGAAAGTGGCTCCTACGAGTCTG

ACAGAGGTCCTATCATTGAGGACCTGAACGCTTAC

GGTGACATTTTTGGCAGCAGTGTGGACCACGCCTA

CGAGACTGTCTGCCTCGCCACCAACAATCAGACTG

CGCTGATCCGCTCGGAAATGGTCTCGGTGGCTCT

ACCCTCGTCAACGGTGGCACCTGGACTCGCCCCCA

CAAGGCACAAGTTGACTCATGGGAGACCGTCTTCG

GAAATGAGGGCTGGAACTGGGACAGCGTGGCCGCC

TACTCCCTCCAGGCTGAGCGTGCTCGCGCACCAAA

TGCCAAACAGATTGCTGCTGGCCACTACTTTAATG

CATCCTGCCATGGTATCAATGGTACTGTCCACGCC

GGACCCCGCGATACCGGTGATGACTACTCCCCCAT

CGTCAAGGCTCTCATGAGCGCTGTCGAAGACAGGG

GCGTTCCCACCAAGAAGGACTTGGGATGCGGTGAC

CCCCATGGTGTGTCCATGTTCCCCAACACCTTGCA

CGAAGACCAAGTGCGCTCTGATGCCGCTCGCGAAT

GGCTCCTCCCCAACTACCAGCGTCCCAACCTGCAA

GTCCTCACTGGACAGTATTGCGGAAAGGTCCTGCT

CAGCCAGAACGCTACCACACCTCGTGCCGTTGGCG

TGGAATTCGGCACCCACAAGGGCAACACCCACAAC

GTCTACGCTAAGCACGAGGTCCTCCTGGCCGCTGG

ATCCGCTGTCTCTCCCACCATCCTCGAATATTCCG

GTATCGGAATGAAGTCCATTCTAGAGCCTCTTGGA

ATTAAGACCGTCGTTGACCTGCCCGTTGGTCTCAA

CCTTCAGGACCAGACCACCTCTACCGTCCGCTCAC

GCATTACCTCCGCCGGTGCCGGACAGGGACAGGCC

GCTTGGTTCGCTACCTTCAACGAGACCTTTGGCGA

CTACACCGAAAAGGCTCACGAGCTGCTCAACACCA

AGCTGGAGCAGTGGGCCGAAGAGGCCGTCGCCCGT

GGCGGATTCCACAACACCACCGCTTTGCTCATCCA

GTACGAGAACTACCGCGACTGGATCGTCAAGGACA

ATGTCGCATACTCGGAACTCTTCCTCGACACGGCC

GGAGAAGCCAGTTTCGATGTGTGGGATCTTCTGCC

CTTCACTAGAGGATACGTCCACATCCTCGACAAGG

ACCCCTACCTCCGCCATTTCGCCTACGACCCTCAG

TACTTCCTCAACGAGCTTGACCTGCTCGGCCAGGC

TGCCGCCACTCAGCTGGCCCGCAACATCTCTAACT

CCGGTGCCATGCAAACTTATTTCGCTGGAGAGACT

ATTCCCGGTGACAACCTCGCGTATGATGCCGACTT

GAGAGCCTGGGTTGAGTATATCCCGTACCACTTCC

GCCCTAACTACCATGGTGTGGGTACTTGCTCCATG

ATGCCGAAGGAGATGGGCGGTGTTGTCGACAATGC

TGCCCGTGTGTATGGTGTGCAGGGACTGCGAGTCA

TCGATGGTTCTATTCCCCCTACGCAGATGTCGTCC

CATGTTATGACGGTCTTTTATGCCATGGCCTTAAA

GATTGCGGATGCCGTCTTGGCGGATTACGCTTCTA

TGCAGTAAGAGGAAGA

GOD-M5-B

SEQ ID NO: 23

SNGIEASLLTDPKEVAGRTVDYIICGGGLTGLTVA

ARLTENPDITVLVIESGSYESDRGPIIEDLNAYGD

IFGSSVDHAYETVCLATNNQTALIRSGNGLGGSTT

LVNGGTWTRPHKAQVDSWETVFGNEGWNWDSVAAY

SLQAERARAPNAKQIAAGHYFNASCHGINGTVHAG

PRDTGDDYSPIVKALMSAVEDRGVPTKKDLGCGDP

HGVSMFPNTLHEDQVRSDAAREWLLPNYQRPNLQV

LTGQYCGKVLLSQNATTPRAVGVEFGTHKGNTHNV

YAKHEVLLAAGSAVSPTILEYSGIGMKSILEPLGI

KTVVDLPVGLNLQDQTTSTVRSRITSAGAGQGQAA

WFATFNETFGDYTEKAHELLNTKLEQWAEEAVARG

GFHNTTALLIQYENYRDWIVKDNVAYSELFLDTAG

EASFDVWDLLPFTRGYVHILDKDPYLRHFAYDPQY

FLNELDLLGQAAATQLARNISNSGAMQTYFAGETI

PGDNLAYDADLRAWVEYIPYHFRPNYHGVGTCSMM

PKEMGGVVDNAARVYGVQGLRVIDGSIPPTQMSSH

VMTVFYAMALKIADAVLADYASMQ

What is claimed is:

1. A thermostable glucose oxidase, containing at least one pair of introduced disulfide bonds in an amino acid sequence of a *Aspergillus niger* glucose oxidase, wherein the introduced disulfide bonds are selected from the group consisting of:
   (A) disulfide bonds formed between an amino acid residue at a position corresponding to position 53 of SEQ ID NO: 1 and an amino acid residue at a position corresponding to position 246 of SEQ ID NO: 1;
   (B) disulfide bonds formed between an amino acid residue at a position corresponding to position 25 of SEQ ID NO: 1 and an amino acid residue at a position corresponding to position 250 of SEQ ID NO: 1;
   (C) disulfide bonds formed between an amino acid residue at a position corresponding to position 20 of SEQ ID NO: 1 and an amino acid residue at a position corresponding to position 45 of SEQ ID NO: 1;
   (D) disulfide bonds formed between an amino acid residue at a position corresponding to position 39 of SEQ ID NO: 1 and an amino acid residue at a position corresponding to position 242 of SEQ ID NO: 1; and
   (E) disulfide bonds formed between an amino acid residue at a position corresponding to position 87 of SEQ ID NO: 1 and an amino acid residue at a position corresponding to position 508 of SEQ ID NO: 1.

2. The thermostable glucose oxidase according to claim 1, wherein the *Aspergillus niger* glucose oxidase is a wild-type *Aspergillus niger* glucose oxidase or a mutant *Aspergillus niger* glucose oxidase.

3. The thermostable glucose oxidase according to claim 2, wherein the amino acid sequence of the wild-type glucose oxidase is set forth in SEQ ID NO: 1; the mutant *Aspergillus niger* glucose oxidase has mutants in at least one position compared with the wild-type *Aspergillus niger* glucose oxidase set forth in SEQ ID NO: 1.

4. The thermostable glucose oxidase according to claim 3, wherein compared with the wild-type *Aspergillus niger* glucose oxidase set forth in SEQ ID NO: 1, the mutant *Aspergillus niger* glucose oxidase has mutants in at least one of the following positions: 14, 16, 25, 30, 34, 37, 43, 45, 53, 67, 84, 90, 92, 94, 96, 106, 121, 135, 141, 142, 162, 167, 204, 246, 259, 315, 332, 362, 405, 406, 420, 446, 449, 453, 477, 501, 504, 506, 509, 510, 521, 526, 528, 536, 554, 560, 572, 575 and 577.

5. The thermostable glucose oxidase according to claim 2, wherein compared with the wild-type *Aspergillus niger* glucose oxidase set forth in SEQ ID NO: 1, the mutant *Aspergillus niger* glucose oxidase has at least one of the following mutants: D14E, S16A, A25V, T30V, T34V, R37K, N43D, S45T, S53C, A67Y, E84C, Q90R, A92Q, 194V, S96F, V106I, S121A, N135S, L141K, Q142K, A162T, V167I, F204L, T246C, G259A, D315K, A332S, S362T, N405K, H406D, V420E, H446R, A449M, Q453N, S477Y, S501R, T504V, Y506W, Y509E, H510N, C521A, K526R, M528L, A536L, T554M, V560L, S572A, 1575V and E577A.

6. The thermostable glucose oxidase according to claim 5, wherein the amino acid sequence of the mutant *Aspergillus niger* glucose oxidase is set forth in SEQ ID NO: 8 or SEQ ID NO: 10.

7. The thermostable glucose oxidase according to claim 1, wherein the amino acid sequence of the thermostable glucose oxidase satisfies at least one, any two, three or all of the items (A), (B), (C) and (E).

8. The thermostable glucose oxidase according to claim 1, wherein the thermostable glucose oxidase comprises an amino acid sequence selected from the group consisting of SEQ ID NO: 11-15, 17, 19, 21 and 23.

9. The thermostable glucose oxidase according to claim 1, wherein the thermostable glucose oxidase is obtained by heterologous expression in a *Pichia pastoris* host.

10. The thermostable glucose oxidase according to claim 1, wherein the amino acid residue capable of forming the disulfide bonds is a cysteine residue or a homocysteine residue.

11. A polynucleotide, encoding the thermostable glucose oxidase according to claim 1.

12. The polynucleotide according to claim 11, wherein a sequence of the polynucleotide encoding the thermostable glucose oxidase is codon-optimized for expression in a *Pichia pastoris*.

13. The polynucleotide according to claim 12, comprising a nucleotide sequence set forth in any one of SEQ ID NO: 3-7, 16, 18, 20 and 22.

14. A host cell, comprising the polynucleotide according to claim 11.

15. The host cell according to claim 14, wherein the host cell is a fungal cell, a bacterial cell, or a plant cell.

16. The host cell according to claim 15, wherein the host cell is a yeast cell or a filamentous fungal cell.

17. The host cell according to claim 16, wherein the host cell is a *Pichia pastoris* cell or an *Aspergillus niger* cell.

* * * * *

SEQUENCE LISTING

<160> NUMBER OF SEQ ID NOS: 23

<210> SEQ ID NO 1
<211> LENGTH: 583
<212> TYPE: PRT
<213> ORGANISM: Aspergillus niger

<400> SEQUENCE: 1

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Thr Gly Leu
            20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365
```

```
Leu Asn Thr Lys Leu Glu Gln Trp Ala Glu Glu Ala Val Ala Arg Gly
    370             375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
                420                 425                 430

Arg Gly Tyr Val His Ile Leu Asp Lys Asp Pro Tyr Leu His His Phe
                435                 440                 445

Ala Tyr Asp Pro Gln Tyr Phe Leu Asn Glu Leu Asp Leu Leu Gly Gln
450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
                500                 505                 510

Pro Asn Tyr His Gly Val Gly Thr Cys Ser Met Met Pro Lys Glu Met
                515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 2
<211> LENGTH: 1766
<212> TYPE: DNA
<213> ORGANISM: Aspergillus niger

<400> SEQUENCE: 2
gaattcagca atggcattga agccagcctc ctgactgatc ccaaggatgt ctccggccgc      60
acggtcgact acatcatcgc tggtggaggt ctgactggac tcaccaccgc tgctcgtctg     120
acggagaacc ccaacatcag tgtgctcgtc atcgaaagtg ctcctacga gtcggacaga      180 ggtcctatca ttgaggacct gaacgcctac ggcgacatct tggcagcag tgtagaccac      240 gcctacgaga ccgtggagct cgctaccaac aatcaaaccg cgctgatccg ctccggaaat     300
ggtctcggtg gctctactct agtgaatggt ggcacctgga ctcgcccca caaggcacag      360 gttgactctt gggagactgt ctttggaaat gagggctgga actgggacaa tgtggccgcc     420
tactccctcc aggctgagcg tgctcgcgca ccaaatgcca acagatcgc tgctggccac      480 tacttcaacg catcctgcca tggtgttaat ggtactgtcc atgccggacc ccgcgacacc     540
ggcgatgact attctcccat cgtcaaggct ctcatgagcg ctgtcgaaga ccggggcgtt     600
cccaccaaga aagacttcgg atgcggtgac ccccatggtg tgtccatgtt ccccaacacc     660
ttgcacgaag accaagtgcg ctccgatgcc gctcgcgaat ggctacttcc caactaccaa     720
cgtcccaacc tgcaagtcct gaccggacag tatgttggta aggtgctcct agccagaac      780 ggcaccaccc tcgtgccgt tggcgtggaa ttcggcaccc acaagggcaa cacccacaac     840
gtttacgcta agcacgaggt cctcctggcc gcgggctccg ctgtctctcc cacaatcctc     900
```

```
gaatattccg gtatcggaat gaagtccatc ctggagcccc ttggtatcga caccgtcgtt      960
gacctgcccg tcggcttgaa cctgcaggac cagaccaccg ctaccgtccg ctcccgcatc     1020
acctctgctg gtgcaggaca gggacaggcc gcttggttcg ccaccttcaa cgagaccttt     1080
ggtgactatt ccgaaaaggc acacgagctg ctcaacacca agctggagca gtgggccgaa     1140
gaggccgtcg cccgtggcgg attccacaac accaccgcct tgctcatcca gtacgagaac     1200
taccgcgact ggattgtcaa ccacaacgtc gcgtactcgg aactcttcct cgacactgcc     1260
ggagtagcca gcttcgatgt gtgggacctt ctgcccttca cccgaggata cgttcacatc     1320
ctcgacaagg accCctacct tcaccacttc gcctacgacc tcagtactt cctcaacgag     1380 ctggacctgc tcggtcaggc tgccgctact caactggccc gcaacatctc caactccggt     1440
gccatgcaga cctacttcgc tggggagact atccccggtg ataacctcgc gtatgatgcc     1500
gatttgagcg cctggactga gtacatcccg taccacttcc gtcctaacta ccatggcgtg     1560
ggtacttgct ccatgatgcc gaaggagatg ggcggtgttg ttgataatgc tgcccgtgtg     1620
tatggtgtgc agggactgcg tgtcattgat ggttctattc ctcctacgca aatgtcgtcc     1680
catgtcatga cggtgttcta tgccatggcg ctaaaaattt cggatgctat cttggaagat     1740
tatgcttcca tgcagtgaga ggaaga                                         1766

<210> SEQ ID NO 3
<211> LENGTH: 1766
<212> TYPE: DNA
<213> ORGANISM: Artificial Sequence
<220> FEATURE:
<223> OTHER INFORMATION: GOD-A

<400> SEQUENCE: 3
gaattcagca atggcattga agccagcctc ctgactgatc ccaaggatgt ctccggccgc       60
acggtcgact acatcatcgc tggtggaggt ctgactggac tcaccaccgc tgctcgtctg      120
acggagaacc ccaacatcag tgtgctcgtc atcgaaagtg gctgctacga gtcggacaga      180
ggtcctatca ttgaggacct gaacgcctac ggcgacatct ttggcagcag tgtagaccac      240
gcctacgaga ccgtggagct cgctaccaac aatcaaaccg cgctgatccg ctccggaaat      300
ggtctcggtg gctctactct agtgaatggt ggcacctgga ctcgccccca caaggcacag      360
gttgactctt gggagactgt cttttggaaa tgagggctgga actgggacaa tgtggccgcc      420
tactccctcc aggctgagcg tgctcgcgca ccaaatgcca aacagatcgc tgctggccac      480
tacttcaacg catcctgcca tggtgttaat ggtactgtcc atgccggacc ccgcgacacc      540
ggcgatgact attctcccat cgtcaaggct ctcatgagcg ctgtcgaaga ccggggcgtt      600
cccaccaaga aagacttcgg atgcggtgac ccccatggtg tgtccatgtt ccccaacacc      660
ttgcacgaag accaagtgcg ctccgatgcc gctcgcgaat ggctacttcc caactaccaa      720
cgtcccaacc tgcaagtcct gtgcggacag tatgttggta aggtgctcct tagccagaac      780
ggcaccaccc ctcgtgccgt tggcgtggaa ttcggcaccc acaagggcaa cacccacaac      840
gtttacgcta agcacgaggt cctcctggcc gcgggctccg ctgtctctcc cacaatcctc      900
gaatattccg gtatcggaat gaagtccatc ctggagcccc ttggtatcga caccgtcgtt      960
gacctgcccg tcggcttgaa cctgcaggac cagaccaccg ctaccgtccg ctcccgcatc     1020
acctctgctg gtgcaggaca gggacaggcc gcttggttcg ccaccttcaa cgagaccttt     1080
ggtgactatt ccgaaaaggc acacgagctg ctcaacacca agctggagca gtgggccgaa     1140
```

| | |
|---|---:|
| gaggccgtcg cccgtggcgg attccacaac accaccgcct tgctcatcca gtacgagaac | 1200 |
| taccgcgact ggattgtcaa ccacaacgtc gcgtactcgg aactcttcct cgacactgcc | 1260 |
| ggagtagcca gcttcgatgt gtgggacctt ctgcccttca cccgaggata cgttcacatc | 1320 |
| ctcgacaagg acccctacct tcaccacttc gcctacgacc ctcagtactt cctcaacgag | 1380 |
| ctggacctgc tcggtcaggc tgccgctact caactggccc gcaacatctc caactccggt | 1440 |
| gccatgcaga cctacttcgc tggggagact atccccggtg ataacctcgc gtatgatgcc | 1500 |
| gatttgagcg cctggactga gtacatcccg taccacttcc gtcctaacta ccatggcgtg | 1560 |
| ggtacttgct ccatgatgcc gaaggagatg ggcggtgttg ttgataatgc tgcccgtgtg | 1620 |
| tatggtgtgc agggactgcg tgtcattgat ggttctattc ctcctacgca aatgtcgtcc | 1680 |
| catgtcatga cggtgttcta tgccatggcg ctaaaaattt cggatgctat cttggaagat | 1740 |
| tatgcttcca tgcagtgaga ggaaga | 1766 |

<210> SEQ ID NO 4
<211> LENGTH: 1766
<212> TYPE: DNA
<213> ORGANISM: Artificial Sequence
<220> FEATURE:
<223> OTHER INFORMATION: GOD-B

<400> SEQUENCE: 4

| | |
|---|---:|
| gaattcagca atggcattga agccagcctc ctgactgatc ccaaggatgt ctccggccgc | 60 |
| acggtcgact acatcatctg cggtggaggt ctgactggac tcaccaccgc tgctcgtctg | 120 |
| acggagaacc ccaacatcag tgtgctcgtc atcgaaagtg gctcctacga gtcggacaga | 180 |
| ggtcctatca ttgaggacct gaacgcctac ggcgacatct ttggcagcag tgtagaccac | 240 |
| gcctacgaga ccgtggagct cgctaccaac aatcaaaccg cgctgatccg ctccggaaat | 300 |
| ggtctcggtg gctctactct agtgaatggt ggcacctgga ctcgcccca caaggcacag | 360 |
| gttgactctt gggagactgt cttggaaat gagggctgga actgggacaa tgtggccgcc | 420 |
| tactccctcc aggctgagcg tgctcgcgca ccaaatgcca acagatcgc tgctggccac | 480 |
| tacttcaacg catcctgcca tggtgttaat ggtactgtcc atgccggacc ccgcgacacc | 540 |
| ggcgatgact attctcccat cgtcaaggct ctcatgagcg ctgtcgaaga ccggggcgtt | 600 |
| cccaccaaga aagacttcgg atgcggtgac ccccatggtg tgtccatgtt ccccaacacc | 660 |
| ttgcacgaag accaagtgcg ctccgatgcc gctcgcgaat ggctacttcc caactaccaa | 720 |
| cgtcccaacc tgcaagtcct gaccggacag tattgcggta aggtgctcct tagccagaac | 780 |
| ggcaccaccc ctcgtgccgt tggcgtggaa ttcggcaccc acaagggcaa cacccacaac | 840 |
| gtttacgcta agcacgaggt cctcctggcc gcggctccg ctgtctctcc cacaatcctc | 900 |
| gaatattccg gtatcggaat gaagtccatc ctggagcccc ttggtatcga caccgtcgtt | 960 |
| gacctgcccg tcggcttgaa cctgcaggac cagaccaccg ctaccgtccg ctcccgcatc | 1020 |
| acctctgctg gtgcaggaca gggacaggcc gcttggttcg ccaccttcaa cgagaccttt | 1080 |
| ggtgactatt ccgaaaaggc cacgagctg ctcaacacca gctggagca gtgggccgaa | 1140 |
| gaggccgtcg cccgtggcgg attccacaac accaccgcct tgctcatcca gtacgagaac | 1200 |
| taccgcgact ggattgtcaa ccacaacgtc gcgtactcgg aactcttcct cgacactgcc | 1260 |
| ggagtagcca gcttcgatgt gtgggacctt ctgcccttca cccgaggata cgttcacatc | 1320 |
| ctcgacaagg acccctacct tcaccacttc gcctacgacc ctcagtactt cctcaacgag | 1380 |
| ctggacctgc tcggtcaggc tgccgctact caactggccc gcaacatctc caactccggt | 1440 |

```
gccatgcaga cctacttcgc tggggagact atccccggtg ataacctcgc gtatgatgcc    1500
gatttgagcg cctggactga gtacatcccg taccacttcc gtcctaacta ccatggcgtg    1560
ggtacttgct ccatgatgcc gaaggagatg ggcggtgttg ttgataatgc tgcccgtgtg    1620
tatggtgtgc agggactgcg tgtcattgat ggttctattc ctcctacgca aatgtcgtcc    1680
catgtcatga cggtgttcta tgccatggcg ctaaaaattt cggatgctat cttggaagat    1740
tatgcttcca tgcagtgaga ggaaga                                        1766

<210> SEQ ID NO 5
<211> LENGTH: 1766
<212> TYPE: DNA
<213> ORGANISM: Artificial Sequence
<220> FEATURE:
<223> OTHER INFORMATION: GOD-C

<400> SEQUENCE: 5
gaattcagca atggcattga agccagcctc ctgactgatc ccaaggatgt ctccggccgc      60
acgtgcgact acatcatcgc tggtggaggt ctgactggac tcaccaccgc tgctcgtctg     120
acggagaacc ccaacatctg cgtgctcgtc atcgaaagtg ctcctacga gtcggacaga     180 ggtcctatca ttgaggacct gaacgcctac ggcgacatct ttggcagcag tgtagaccac     240
gcctacgaga ccgtggagct cgctaccaac aatcaaaccg cgctgatccg ctccggaaat     300
ggtctcggtg gctctactct agtgaatggt ggcacctgga ctcgccccca caaggcacag     360
gttgactctt gggagactgt ctttggaaat gagggctgga actgggacaa tgtggccgcc     420
tactccctcc aggctgagcg tgctcgcgca ccaaatgcca acagatcgc tgctggccac     480 tacttcaacg catcctgcca tggtgttaat ggtactgtcc atgccggacc ccgcgacacc     540
ggcgatgact attctcccat cgtcaaggct ctcatgagcg ctgtcgaaga ccggggcgtt     600
cccaccaaga aagacttcgg atgcggtgac ccccatggtg tgtccatgtt ccccaacacc     660
ttgcacgaag accaagtgcg ctccgatgcc gctcgcgaat ggctacttcc caactaccaa     720
cgtcccaacc tgcaagtcct gaccggacag tatgttggta aggtgctcct tagccagaac     780
ggcaccaccc ctcgtgccgt tggcgtggaa ttcggcaccc acaagggcaa cacccacaac     840
gtttacgcta agcacgaggt cctcctggcc gcgggctccg ctgtctctcc cacaatcctc     900
gaatattccg gtatcggaat gaagtccatc ctggagcccc ttggtatcga caccgtcgtt     960
gacctgcccg tcggcttgaa cctgcaggac cagaccaccg ctaccgtccg ctcccgcatc    1020
acctctgctg gtgcaggaca gggacaggcc gcttggttcg ccaccttcaa cgagaccttt    1080
ggtgactatt ccgaaaaggc acacgagctg ctcaacacca agctggagca gtgggccgaa    1140
gaggccgtcg cccgtggcgg attccacaac accaccgcct tgctcatcca gtacgagaac    1200
taccgcgact ggattgtcaa ccacaacgtc gcgtactcgg aactcttcct cgacactgcc    1260
ggagtagcca gcttcgatgt gtgggacctt ctgcccttca cccgaggata cgttcacatc    1320
ctcgacaagg accctacct tcaccacttc gcctacgacc ctcagtactt cctcaacgag    1380
ctggacctgc tcggtcaggc tgccgctact caactggccc gcaacatctc caactccggt    1440
gccatgcaga cctacttcgc tggggagact atccccggtg ataacctcgc gtatgatgcc    1500
gatttgagcg cctggactga gtacatcccg taccacttcc gtcctaacta ccatggcgtg    1560
ggtacttgct ccatgatgcc gaaggagatg ggcggtgttg ttgataatgc tgcccgtgtg    1620
tatggtgtgc agggactgcg tgtcattgat ggttctattc ctcctacgca aatgtcgtcc    1680
```

<210> SEQ ID NO 6
<211> LENGTH: 1766
<212> TYPE: DNA
<213> ORGANISM: Artificial Sequence
<220> FEATURE:
<223> OTHER INFORMATION: GOD-D

<400> SEQUENCE: 6

```
gaattcagca atggcattga agccagcctc ctgactgatc ccaaggatgt ctccggccgc      60
acggtcgact acatcatcgc tggtggaggt ctgactggac tcaccaccgc tgctcgtctg     120
tgcgagaacc ccaacatcag tgtgctcgtc atcgaaagtg ctcctacga gtcggacaga     180
ggtcctatca ttgaggacct gaacgcctac ggcgacatct ttggcagcag tgtagaccac     240
gcctacgaga ccgtggagct cgctaccaac aatcaaaccg cgctgatccg ctccggaaat     300
ggtctcggtg gctctactct agtgaatggt ggcacctgga ctcgccccca caaggcacag     360
gttgactctt gggagactgt ctttggaaat gagggctgga actgggacaa tgtggccgcc     420
tactccctcc aggctgagcg tgctcgcgca ccaaatgcca acagatcgc tgctggccac     480
tacttcaacg catcctgcca tggtgttaat ggtactgtcc atgccggacc ccgcgacacc     540
ggcgatgact attctcccat cgtcaaggct ctcatgagcg ctgtcgaaga ccggggcgtt     600
cccaccaaga aagacttcgg atgcggtgac ccccatggtg tgtccatgtt ccccaacacc     660
ttgcacgaag accaagtgcg ctccgatgcc gctcgcgaat ggctacttcc caactaccaa     720
cgtcccaact gccaagtcct gaccggacag tatgttggta aggtgctcct agccagaac     780
ggcaccaccc tcgtgccgt tggcgtgaa ttcggcaccc acaagggcaa cacccacaac     840
gtttacgcta agcacgaggt cctcctggcc gcgggctccg ctgtctctcc cacaatcctc     900
gaatattccg gtatcggaat gaagtccatc ctggagcccc ttggtatcga caccgtcgtt     960
gacctgcccg tcggcttgaa cctgcaggac cagaccaccg ctaccgtccg ctcccgcatc    1020
acctctgctg gtgcaggaca gggacaggcc gcttggttcg ccaccttcaa cgagaccttt    1080
ggtgactatt ccgaaaaggc acacgagctg ctcaacacca agctggagca gtgggccgaa    1140
gaggccgtcg cccgtggcgg attccacaac accaccgcct tgctcatcca gtacgagaac    1200
taccgcgact ggattgtcaa ccacaacgtc gcgtactcgg aactcttcct cgacactgcc    1260
ggagtagcca gcttcgatgt gtgggacctt ctgcccttca cccgaggata cgttcacatc    1320
ctcgacaagg accctacct tcaccactc gcctacgacc tcagtactt cctcaacgag    1380
ctggacctgc tcgtcaggc tgccgctact caactggccc gcaacatctc caactccggt    1440
gccatgcaga cctacttcgc tggggagact atccccggtg ataacctcgc gtatgatgcc    1500
gatttgagcg cctggactga gtacatcccg taccacttcc gtcctaacta ccatggcgtg    1560
ggtacttgct ccatgatgcc gaaggagatg ggcggtgttg ttgataatgc tgcccgtgtg    1620
tatggtgtgc agggactgcg tgtcattgat ggttctattc ctcctacgca aatgtcgtcc    1680
catgtcatga cggtgttcta tgccatggcg ctaaaaattt cggatgctat cttggaagat    1740
tatgcttcca tgcagtgaga ggaaga                                         1766
```

<210> SEQ ID NO 7
<211> LENGTH: 1766
<212> TYPE: DNA
<213> ORGANISM: Artificial Sequence

<220> FEATURE:
<223> OTHER INFORMATION: GOD-E

<400> SEQUENCE: 7

```
gaattcagca atggcattga agccagcctc ctgactgatc ccaaggatgt ctccggccgc      60
acggtcgact acatcatcgc tgtggaggt ctgactggac tcaccaccgc tgctcgtctg     120
acggagaacc ccaacatcag tgtgctcgtc atcgaaagtg gctcctacga gtcggacaga    180
ggtcctatca ttgaggacct gaacgcctac ggcgacatct ttggcagcag tgtagaccac    240
gcctacgaga ccgtggagct cgcttgcaac aatcaaaccg cgctgatccg ctccggaaat    300
ggtctcggtg gctctactct agtgaatggt ggcacctgga ctcgccccca caaggcacag    360
gttgactctt gggagactgt ctttggaaat gagggctgga actgggacaa tgtggccgcc    420
tactccctcc aggctgagcg tgctcgcgca ccaaatgcca acagatcgc tgctggccac     480
tacttcaacg catcctgcca tggtgttaat ggtactgtcc atgccggacc ccgcgacacc    540
ggcgatgact attctcccat cgtcaaggct ctcatgagcg ctgtcgaaga ccggggcgtt    600
cccaccaaga aagacttcgg atgcggtgac ccccatggtg tgtccatgtt ccccaacacc    660
ttgcacgaag accaagtgcg ctccgatgcc gctcgcgaat ggctacttcc caactaccaa    720
cgtcccaacc tgcaagtcct gaccggacag tatgttggta aggtgctcct tagccagaac    780
ggcaccaccc ctcgtgccgt tggcgtggaa ttcggcaccc acaagggcaa cacccacaac    840
gtttacgcta agcacgaggt cctcctggcc gcgggctccg ctgtctctcc cacaatcctc    900
gaatattccg gtatcggaat gaagtccatc ctggagcccc ttggtatcga caccgtcgtt    960
gacctgcccg tcggcttgaa cctgcaggac cagaccaccg ctaccgtccg ctcccgcatc   1020
acctctgctg gtgcaggaca gggacaggcc gcttggttcg ccaccttcaa cgagaccttt   1080
ggtgactatt ccgaaaaggc acacgagctg ctcaacacca gctggagca gtgggccgaa    1140
gaggccgtcg cccgtggcgg attccacaac accaccgcct tgctcatcca gtacgagaac   1200
taccgcgact ggattgtcaa ccacaacgtc gcgtactcgg aactcttcct cgacactgcc   1260
ggagtagcca gcttcgatgt gtgggacctt ctgcccttca cccgaggata cgttcacatc   1320
ctcgacaagg accctacct tcaccactc gcctacgacc tcagtactt cctcaacgag      1380
ctggacctgc tcggtcaggc tgccgctact caactggccc gcaacatctc caactccggt   1440
gccatgcaga cctacttcgc tggggagact atccccggtg ataacctcgc gtatgatgcc   1500
gatttgagcg cctggactga gtacatctgc taccacttcc gtcctaacta ccatggcgtg   1560
ggtacttgct ccatgatgcc gaaggagatg ggcggtgttg ttgataatgc tgcccgtgtg   1620
tatggtgtgc agggactgcg tgtcattgat ggttctattc ctcctacgca aatgtcgtcc   1680
catgtcatga cggtgttcta tgccatggcg ctaaaatttt cggatgctat cttggaagat   1740
tatgcttcca tgcagtgaga ggaaga                                        1766
```

<210> SEQ ID NO 8
<211> LENGTH: 583
<212> TYPE: PRT
<213> ORGANISM: Artificial Sequence
<220> FEATURE:
<223> OTHER INFORMATION: F19

<400> SEQUENCE: 8

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Val Gly Leu

```
                20              25              30
Thr Thr Ala Ala Lys Leu Thr Glu Asn Pro Asn Ile Ser Val Leu Val
            35              40              45
Ile Glu Ser Gly Ser Tyr Glu Ser Asp Arg Gly Pro Ile Ile Glu Asp
 50              55              60
Leu Asn Ala Tyr Gly Asp Ile Phe Gly Ser Ser Val Asp His Ala Tyr
 65              70              75              80
Glu Thr Val Glu Leu Ala Thr Asn Asn Gln Thr Ala Leu Val Arg Ser
                85              90              95
Gly Asn Gly Leu Gly Gly Ser Thr Leu Ile Asn Gly Gly Thr Trp Thr
            100             105             110
Arg Pro His Lys Ala Gln Val Asp Ser Trp Glu Thr Val Phe Gly Asn
            115             120             125
Glu Gly Trp Asn Trp Asp Asn Val Ala Ala Tyr Ser Leu Gln Ala Glu
            130             135             140
Arg Ala Arg Ala Pro Asn Ala Lys Gln Ile Ala Ala Gly His Tyr Phe
145             150             155             160
Asn Thr Ser Cys His Gly Val Asn Gly Thr Val His Ala Gly Pro Arg
            165             170             175
Asp Thr Gly Asp Asp Tyr Ser Pro Ile Val Lys Ala Leu Met Ser Ala
            180             185             190
Val Glu Asp Arg Gly Val Pro Thr Lys Lys Asp Phe Gly Cys Gly Asp
            195             200             205
Pro His Gly Val Ser Met Phe Pro Asn Thr Leu His Glu Asp Gln Val
            210             215             220
Arg Ser Asp Ala Ala Arg Glu Trp Leu Leu Pro Asn Tyr Gln Arg Pro
225             230             235             240
Asn Leu Gln Val Leu Thr Gly Gln Tyr Val Gly Lys Val Leu Leu Ser
            245             250             255
Gln Asn Gly Thr Thr Pro Arg Ala Val Gly Val Glu Phe Gly Thr His
            260             265             270
Lys Gly Asn Thr His Asn Val Tyr Ala Lys His Glu Val Leu Leu Ala
            275             280             285
Ala Gly Ser Ala Val Ser Pro Thr Ile Leu Glu Tyr Ser Gly Ile Gly
            290             295             300
Met Lys Ser Ile Leu Glu Pro Leu Gly Ile Asp Thr Val Val Asp Leu
305             310             315             320
Pro Val Gly Leu Asn Leu Gln Asp Gln Thr Thr Ala Thr Val Arg Ser
            325             330             335
Arg Ile Thr Ser Ala Gly Ala Gly Gln Gly Gln Ala Ala Trp Phe Ala
            340             345             350
Thr Phe Asn Glu Thr Phe Gly Asp Tyr Ser Glu Lys Ala His Glu Leu
            355             360             365
Leu Asn Thr Lys Leu Glu Gln Trp Ala Glu Glu Ala Val Ala Arg Gly
            370             375             380
Gly Phe His Asn Thr Thr Ala Leu Leu Ile Gln Tyr Glu Asn Tyr Arg
385             390             395             400
Asp Trp Ile Val Asn His Asn Val Ala Tyr Ser Glu Leu Phe Leu Asp
            405             410             415
Thr Ala Gly Val Ala Ser Phe Asp Val Trp Asp Leu Leu Pro Phe Thr
            420             425             430
Arg Gly Tyr Val His Ile Leu Asp Lys Asp Pro Tyr Leu His His Phe
            435             440             445
```

```
Ala Tyr Asp Pro Gln Tyr Phe Leu Asn Glu Leu Asp Leu Leu Gly Gln
            450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
                500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
        530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 9
<211> LENGTH: 583
<212> TYPE: PRT
<213> ORGANISM: Aspergillus niger

<400> SEQUENCE: 9

Ser Asn Gly Ile Glu Ala Ser Leu Leu Thr Asp Pro Lys Glu Val Ala
1               5                   10                  15

Gly Arg Thr Val Asp Tyr Ile Ile Ala Gly Gly Gly Leu Thr Gly Leu
            20                  25                  30

Thr Thr Ala Ala Arg Leu Thr Glu Asn Pro Asp Ile Thr Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Ser Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Ile Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Leu Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
```

```
            225                 230                 235                 240
        Asn Leu Gln Val Leu Thr Gly Gln Tyr Val Gly Lys Val Leu Leu Ser
                        245                 250                 255

Gln Asn Ala Thr Thr Pro Arg Ala Val Gly Val Glu Phe Gly Thr His
                    260                 265                 270

Lys Gly Asn Thr His Asn Val Tyr Ala Lys His Glu Val Leu Leu Ala
                    275                 280                 285

Ala Gly Ser Ala Val Ser Pro Thr Ile Leu Glu Tyr Ser Gly Ile Gly
                    290                 295                 300

Met Lys Ser Ile Leu Glu Pro Leu Gly Ile Asp Thr Val Val Asp Leu
        305                 310                 315                 320

Pro Val Gly Leu Asn Leu Gln Asp Gln Thr Thr Ser Thr Val Arg Ser
                        325                 330                 335

Arg Ile Thr Ser Ala Gly Ala Gly Gln Gly Gln Ala Ala Trp Phe Ala
                    340                 345                 350

Thr Phe Asn Glu Thr Phe Gly Asp Tyr Thr Glu Lys Ala His Glu Leu
                    355                 360                 365

Leu Asn Thr Lys Leu Glu Gln Trp Ala Glu Ala Val Ala Arg Gly
                370                 375                 380

Gly Phe His Asn Thr Thr Ala Leu Leu Ile Gln Tyr Glu Asn Tyr Arg
        385                 390                 395                 400

Asp Trp Ile Val Lys Asp Asn Val Ala Tyr Ser Glu Leu Phe Leu Asp
                        405                 410                 415

Thr Ala Gly Val Ala Ser Phe Asp Val Trp Asp Leu Leu Pro Phe Thr
                    420                 425                 430

Arg Gly Tyr Val His Ile Leu Asp Lys Asp Pro Tyr Leu Arg His Phe
                    435                 440                 445

Ala Tyr Asp Pro Gln Tyr Phe Leu Asn Glu Leu Asp Leu Leu Gly Gln
                    450                 455                 460

Ala Ala Ala Thr Gln Leu Ala Arg Asn Ile Ser Asn Ser Gly Ala Met
        465                 470                 475                 480

Gln Thr Tyr Phe Ala Gly Glu Thr Ile Pro Gly Asp Asn Leu Ala Tyr
                        485                 490                 495

Asp Ala Asp Leu Arg Ala Trp Val Glu Tyr Ile Pro Tyr Asn Phe Arg
                    500                 505                 510

Pro Asn Tyr His Gly Val Gly Thr Cys Ser Met Met Pro Lys Glu Met
                    515                 520                 525

Gly Gly Val Val Asp Asn Ala Ala Arg Val Tyr Gly Val Gln Gly Leu
                    530                 535                 540

Arg Val Ile Asp Gly Ser Ile Pro Pro Thr Gln Met Ser Ser His Val
        545                 550                 555                 560

Met Thr Val Phe Tyr Ala Met Ala Leu Lys Ile Ala Asp Ala Val Leu
                        565                 570                 575

Ala Asp Tyr Ala Ser Met Gln
                    580

<210> SEQ ID NO 10
<211> LENGTH: 583
<212> TYPE: PRT
<213> ORGANISM: Artificial Sequence
<220> FEATURE:
<223> OTHER INFORMATION: GOD-M5

<400> SEQUENCE: 10

Ser Asn Gly Ile Glu Ala Ser Leu Leu Thr Asp Pro Lys Glu Val Ala
```

-continued

|     |     |     |     |     |     |     |     |     |     |     |     |     |     |     |
|-----|-----|-----|-----|-----|-----|-----|-----|-----|-----|-----|-----|-----|-----|-----|
| 1 | | | | 5 | | | | | 10 | | | | | 15 |

Gly Arg Thr Val Asp Tyr Ile Ile Ala Gly Gly Leu Thr Gly Leu
                20                      25                      30

Thr Val Ala Ala Arg Leu Thr Glu Asn Pro Asp Ile Thr Val Leu Val
                35                      40                      45

Ile Glu Ser Gly Ser Tyr Glu Ser Asp Arg Gly Pro Ile Ile Glu Asp
                50                      55                      60

Leu Asn Ala Tyr Gly Asp Ile Phe Gly Ser Ser Val Asp His Ala Tyr
65                      70                      75                      80

Glu Thr Val Cys Leu Ala Thr Asn Asn Gln Thr Ala Leu Ile Arg Ser
                        85                      90                      95

Gly Asn Gly Leu Gly Gly Ser Thr Leu Val Asn Gly Gly Thr Trp Thr
                        100                     105                     110

Arg Pro His Lys Ala Gln Val Asp Ser Trp Glu Thr Val Phe Gly Asn
                        115                     120                     125

Glu Gly Trp Asn Trp Asp Ser Val Ala Ala Tyr Ser Leu Gln Ala Glu
                        130                     135                     140

Arg Ala Arg Ala Pro Asn Ala Lys Gln Ile Ala Ala Gly His Tyr Phe
145                     150                     155                     160

Asn Ala Ser Cys His Gly Ile Asn Gly Thr Val His Ala Gly Pro Arg
                        165                     170                     175

Asp Thr Gly Asp Asp Tyr Ser Pro Ile Val Lys Ala Leu Met Ser Ala
                        180                     185                     190

Val Glu Asp Arg Gly Val Pro Thr Lys Lys Asp Leu Gly Cys Gly Asp
                        195                     200                     205

Pro His Gly Val Ser Met Phe Pro Asn Thr Leu His Glu Asp Gln Val
                        210                     215                     220

Arg Ser Asp Ala Ala Arg Glu Trp Leu Leu Pro Asn Tyr Gln Arg Pro
225                     230                     235                     240

Asn Leu Gln Val Leu Thr Gly Gln Tyr Val Gly Lys Val Leu Leu Ser
                        245                     250                     255

Gln Asn Ala Thr Thr Pro Arg Ala Val Gly Val Glu Phe Gly Thr His
                        260                     265                     270

Lys Gly Asn Thr His Asn Val Tyr Ala Lys His Glu Val Leu Leu Ala
                        275                     280                     285

Ala Gly Ser Ala Val Ser Pro Thr Ile Leu Glu Tyr Ser Gly Ile Gly
                        290                     295                     300

Met Lys Ser Ile Leu Glu Pro Leu Gly Ile Lys Thr Val Val Asp Leu
305                     310                     315                     320

Pro Val Gly Leu Asn Leu Gln Asp Gln Thr Thr Ser Thr Val Arg Ser
                        325                     330                     335

Arg Ile Thr Ser Ala Gly Ala Gly Gln Gly Gln Ala Ala Trp Phe Ala
                        340                     345                     350

Thr Phe Asn Glu Thr Phe Gly Asp Tyr Thr Glu Lys Ala His Glu Leu
                        355                     360                     365

Leu Asn Thr Lys Leu Glu Gln Trp Ala Glu Glu Ala Val Ala Arg Gly
                        370                     375                     380

Gly Phe His Asn Thr Thr Ala Leu Leu Ile Gln Tyr Glu Asn Tyr Arg
385                     390                     395                     400

Asp Trp Ile Val Lys Asp Asn Val Ala Tyr Ser Glu Leu Phe Leu Asp
                        405                     410                     415

Thr Ala Gly Glu Ala Ser Phe Asp Val Trp Asp Leu Leu Pro Phe Thr
                        420                     425                     430

```
Arg Gly Tyr Val His Ile Leu Asp Lys Asp Pro Tyr Leu Arg His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Arg Ala Trp Val Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ala Asp Ala Val Leu
                565                 570                 575

Ala Asp Tyr Ala Ser Met Gln
            580

<210> SEQ ID NO 11
<211> LENGTH: 583
<212> TYPE: PRT
<213> ORGANISM: Artificial Sequence
<220> FEATURE:
<223> OTHER INFORMATION: GOD-A

<400> SEQUENCE: 11

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Thr Gly Leu
            20                  25                  30

Thr Thr Ala Ala Arg Leu Thr Glu Asn Pro Asn Ile Ser Val Leu Val
        35                  40                  45

Ile Glu Ser Gly Cys Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205
```

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Cys Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Ala Val Ala Arg Gly
370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 12
<211> LENGTH: 583
<212> TYPE: PRT
<213> ORGANISM: Artificial Sequence
<220> FEATURE:

<223> OTHER INFORMATION: GOD-B

<400> SEQUENCE: 12

```
Ser Asn Gly Ile Glu Ala Ser Leu Leu Thr Asp Pro Lys Asp Val Ser
1               5                   10                  15

Gly Arg Thr Val Asp Tyr Ile Ile Cys Gly Gly Gly Leu Thr Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Cys Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Glu Ala Val Ala Arg Gly
370                 375                 380

Gly Phe His Asn Thr Thr Ala Leu Leu Ile Gln Tyr Glu Asn Tyr Arg
385                 390                 395                 400
```

-continued

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Ser Ala Trp Thr Glu Tyr Ile Pro Tyr His Phe Arg
        500                 505                 510

Pro Asn Tyr His Gly Val Gly Thr Cys Ser Met Met Pro Lys Glu Met
    515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
            565                 570                 575

Glu Asp Tyr Ala Ser Met Gln
            580

<210> SEQ ID NO 13
<211> LENGTH: 583
<212> TYPE: PRT
<213> ORGANISM: Artificial Sequence
<220> FEATURE:
<223> OTHER INFORMATION: GOD-C

<400> SEQUENCE: 13

Ser Asn Gly Ile Glu Ala Ser Leu Leu Thr Asp Pro Lys Asp Val Ser
1               5                   10                  15

Gly Arg Thr Cys Asp Tyr Ile Ile Ala Gly Gly Leu Thr Gly Leu
            20                  25                  30

Thr Thr Ala Ala Arg Leu Thr Glu Asn Pro Asn Ile Cys Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
            85                  90                  95

Gly Asn Gly Leu Gly Gly Ser Thr Leu Val Asn Gly Gly Thr Trp Thr
        100                 105                 110

Arg Pro His Lys Ala Gln Val Asp Ser Trp Glu Thr Val Phe Gly Asn
    115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
            165                 170                 175

```
Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580
```

<210> SEQ ID NO 14
<211> LENGTH: 583
<212> TYPE: PRT
<213> ORGANISM: Artificial Sequence
<220> FEATURE:
<223> OTHER INFORMATION: GOD-D

<400> SEQUENCE: 14

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Thr Gly Leu
            20                  25                  30

Thr Thr Ala Ala Arg Leu Cys Glu Asn Pro Asn Ile Ser Val Leu Val
            35                  40                  45

Ile Glu Ser Gly Ser Tyr Glu Ser Asp Arg Gly Pro Ile Ile Glu Asp
50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
            195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Cys Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Glu Ala Val Ala Arg Gly
```

```
                370                 375                 380
Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
                420                 425                 430

Arg Gly Tyr Val His Ile Leu Asp Lys Asp Pro Tyr Leu His His Phe
                435                 440                 445

Ala Tyr Asp Pro Gln Tyr Phe Leu Asn Glu Leu Asp Leu Leu Gly Gln
                450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
                500                 505                 510

Pro Asn Tyr His Gly Val Gly Thr Cys Ser Met Met Pro Lys Glu Met
                515                 520                 525

Gly Gly Val Val Asp Asn Ala Ala Arg Val Tyr Gly Val Gln Gly Leu
                530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
                580

<210> SEQ ID NO 15
<211> LENGTH: 583
<212> TYPE: PRT
<213> ORGANISM: Artificial Sequence
<220> FEATURE:
<223> OTHER INFORMATION: GOD-E

<400> SEQUENCE: 15

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Thr Gly Leu
                20                  25                  30

Thr Thr Ala Ala Arg Leu Thr Glu Asn Pro Asn Ile Ser Val Leu Val
                35                  40                  45

Ile Glu Ser Gly Ser Tyr Glu Ser Asp Arg Gly Pro Ile Ile Glu Asp
                50                  55                  60

Leu Asn Ala Tyr Gly Asp Ile Phe Gly Ser Ser Val Asp His Ala Tyr
65                  70                  75                  80

Glu Thr Val Glu Leu Ala Cys Asn Asn Gln Thr Ala Leu Ile Arg Ser
                85                  90                  95

Gly Asn Gly Leu Gly Gly Ser Thr Leu Val Asn Gly Gly Thr Trp Thr
                100                 105                 110

Arg Pro His Lys Ala Gln Val Asp Ser Trp Glu Thr Val Phe Gly Asn
                115                 120                 125

Glu Gly Trp Asn Trp Asp Asn Val Ala Ala Tyr Ser Leu Gln Ala Glu
                130                 135                 140

Arg Ala Arg Ala Pro Asn Ala Lys Gln Ile Ala Ala Gly His Tyr Phe
```

```
           145                 150                 155                 160
Asn Ala Ser Cys His Gly Val Asn Gly Thr Val His Ala Gly Pro Arg
               165                 170                 175
Asp Thr Gly Asp Asp Tyr Ser Pro Ile Val Lys Ala Leu Met Ser Ala
               180                 185                 190
Val Glu Asp Arg Gly Val Pro Thr Lys Lys Asp Phe Gly Cys Gly Asp
               195                 200                 205
Pro His Gly Val Ser Met Phe Pro Asn Thr Leu His Glu Asp Gln Val
           210                 215                 220
Arg Ser Asp Ala Ala Arg Glu Trp Leu Leu Pro Asn Tyr Gln Arg Pro
225                 230                 235                 240
Asn Leu Gln Val Leu Thr Gly Gln Tyr Val Gly Lys Val Leu Leu Ser
               245                 250                 255
Gln Asn Gly Thr Thr Pro Arg Ala Val Gly Val Glu Phe Gly Thr His
               260                 265                 270
Lys Gly Asn Thr His Asn Val Tyr Ala Lys His Glu Val Leu Leu Ala
           275                 280                 285
Ala Gly Ser Ala Val Ser Pro Thr Ile Leu Glu Tyr Ser Gly Ile Gly
           290                 295                 300
Met Lys Ser Ile Leu Glu Pro Leu Gly Ile Asp Thr Val Val Asp Leu
305                 310                 315                 320
Pro Val Gly Leu Asn Leu Gln Asp Gln Thr Thr Ala Thr Val Arg Ser
               325                 330                 335
Arg Ile Thr Ser Ala Gly Ala Gly Gln Gly Gln Ala Ala Trp Phe Ala
               340                 345                 350
Thr Phe Asn Glu Thr Phe Gly Asp Tyr Ser Glu Lys Ala His Glu Leu
           355                 360                 365
Leu Asn Thr Lys Leu Glu Gln Trp Ala Glu Glu Ala Val Ala Arg Gly
           370                 375                 380
Gly Phe His Asn Thr Thr Ala Leu Leu Ile Gln Tyr Glu Asn Tyr Arg
385                 390                 395                 400
Asp Trp Ile Val Asn His Asn Val Ala Tyr Ser Glu Leu Phe Leu Asp
               405                 410                 415
Thr Ala Gly Val Ala Ser Phe Asp Val Trp Asp Leu Leu Pro Phe Thr
               420                 425                 430
Arg Gly Tyr Val His Ile Leu Asp Lys Asp Pro Tyr Leu His His Phe
               435                 440                 445
Ala Tyr Asp Pro Gln Tyr Phe Leu Asn Glu Leu Asp Leu Leu Gly Gln
           450                 455                 460
Ala Ala Ala Thr Gln Leu Ala Arg Asn Ile Ser Asn Ser Gly Ala Met
465                 470                 475                 480
Gln Thr Tyr Phe Ala Gly Glu Thr Ile Pro Gly Asp Asn Leu Ala Tyr
               485                 490                 495
Asp Ala Asp Leu Ser Ala Trp Thr Glu Tyr Ile Cys Tyr His Phe Arg
               500                 505                 510
Pro Asn Tyr His Gly Val Gly Thr Cys Ser Met Met Pro Lys Glu Met
           515                 520                 525
Gly Gly Val Val Asp Asn Ala Ala Arg Val Tyr Gly Val Gln Gly Leu
           530                 535                 540
Arg Val Ile Asp Gly Ser Ile Pro Pro Thr Gln Met Ser Ser His Val
545                 550                 555                 560
Met Thr Val Phe Tyr Ala Met Ala Leu Lys Ile Ser Asp Ala Ile Leu
               565                 570                 575
```

Glu Asp Tyr Ala Ser Met Gln
             580

<210> SEQ ID NO 16
<211> LENGTH: 1766
<212> TYPE: DNA
<213> ORGANISM: Artificial Sequence
<220> FEATURE:
<223> OTHER INFORMATION: F19-A

<400> SEQUENCE: 16

| | | | | | |
|---|---|---|---|---|---|
| gaattcagca | atggcattga | agccagcctc | ctgactgatc | ccaaggatgt | ctccggccgc | 60 |
| acggtcgact | acatcatcgc | tggtggaggt | ctggtgggac | tcaccaccgc | tgctaagctg | 120 |
| acggagaacc | ccaacatcag | tgtgctcgtc | atcgaaagtg | gctgctacga | gtcggacaga | 180 |
| ggtcctatca | ttgaggacct | gaacgcctac | ggcgacatct | ttggcagcag | gtagaccac | 240 |
| gcctacgaga | ccgtggagct | cgctaccaac | aatcaaaccg | cgctggtgcg | ctccggaaat | 300 |
| ggtctcggtg | gctctactct | aatcaatggt | ggcacctgga | ctcgccccca | caaggcacag | 360 |
| gttgactctt | gggagactgt | ctttggaaat | gagggctgga | actgggacaa | tgtggccgcc | 420 |
| tactccctcc | aggctgagcg | tgctcgcgca | ccaaatgcca | acagatcgc | tgctggccac | 480 |
| tacttcaaca | cctcctgcca | tggtgttaat | ggtactgtcc | atgccggacc | ccgcgacacc | 540 |
| ggcgatgact | attctcccat | cgtcaaggct | ctcatgagcg | ctgtcgaaga | ccggggcgtt | 600 |
| cccaccaaga | aagacttcgg | atgcggtgac | ccccatggtg | tgtccatgtt | ccccaacacc | 660 |
| ttgcacgaag | accaagtgcg | ctccgatgcc | gctcgcgaat | ggctacttcc | caactaccaa | 720 |
| cgtcccaacc | tgcaagtcct | gtgcggacag | tatgttggta | aggtgctcct | tagccagaac | 780 |
| ggcaccaccc | tcgtgccgt | tggcgtggaa | ttcggcaccc | acaagggcaa | cacccacaac | 840 |
| gtttacgcta | agcacgaggt | cctcctggcc | gcgggctccg | ctgtctctcc | cacaatcctc | 900 |
| gaatattccg | gtatcggaat | gaagtccatc | ctggagcccc | ttggtatcga | caccgtcgtt | 960 |
| gacctgcccg | tcggcttgaa | cctgcaggac | cagaccaccg | ctaccgtccg | ctcccgcatc | 1020 |
| acctctgctg | gtgcaggaca | gggacaggcc | gcttggttcg | ccaccttcaa | cgagaccttt | 1080 |
| ggtgactatt | ccgaaaaggc | cacgagctg | ctcaacacca | agctggagca | gtgggccgaa | 1140 |
| gaggccgtcg | cccgtggcgg | attccacaac | accaccgcct | tgctcatcca | gtacgagaac | 1200 |
| taccgcgact | ggattgtcaa | ccacaacgtc | gcgtactcgg | aactcttcct | cgacactgcc | 1260 |
| ggagtagcca | gcttcgatgt | gtgggacctt | ctgcccttca | cccgaggata | cgttcacatc | 1320 |
| ctcgacaagg | acccctacct | tcaccacttc | gcctacgacc | tcagtactt | cctcaacgag | 1380 |
| ctggacctgc | tcggtcaggc | tgccgctact | caactggccc | gcaacatctc | caactccggt | 1440 |
| gccatgcaga | cctacttcgc | tggggagact | atccccggtg | ataacctcgc | gtatgatgcc | 1500 |
| gatttgagcg | cctggactga | gtacatcccg | taccacttcc | gtcctaacta | ccatggcgtg | 1560 |
| ggtacttgct | ccatgatgcc | gaaggagatg | ggcggtgttg | ttgataatgc | tgcccgtgtg | 1620 |
| tatggtgtgc | agggactgcg | tgtcattgat | ggttctattc | ctcctacgca | aatgtcgtcc | 1680 |
| catgtcatga | cggtgttcta | tgccatggcg | ctaaaaattt | cggatgctat | cttggaagat | 1740 |
| tatgcttcca | tgcagtgaga | ggaaga | | | | 1766 |

<210> SEQ ID NO 17
<211> LENGTH: 583
<212> TYPE: PRT
<213> ORGANISM: Artificial Sequence

```
<220> FEATURE:
<223> OTHER INFORMATION: F19-A

<400> SEQUENCE: 17

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Lys Leu Thr Glu Asn Pro Asn Ile Ser Val Leu Val
            35                  40                  45

Ile Glu Ser Gly Cys Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Ile Asn Gly Gly Thr Trp Thr
            100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Thr Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
            195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Cys Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Glu Ala Val Ala Arg Gly
370                 375                 380

Gly Phe His Asn Thr Thr Ala Leu Leu Ile Gln Tyr Glu Asn Tyr Arg
385                 390                 395                 400
```

Asp Trp Ile Val Asn His Asn Val Ala Tyr Ser Glu Leu Phe Leu Asp
            405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
            450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
            530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
            565                 570                 575

Glu Asp Tyr Ala Ser Met Gln
            580

<210> SEQ ID NO 18
<211> LENGTH: 1766
<212> TYPE: DNA
<213> ORGANISM: Artificial Sequence
<220> FEATURE:
<223> OTHER INFORMATION: F19-B

<400> SEQUENCE: 18

```
gaattcagca atggcattga agccagcctc ctgactgatc ccaaggatgt ctccggccgc    60
acggtcgact acatcatctg cggtggaggt ctggtgggac tcaccaccgc tgctaagctg   120
acggagaacc ccaacatcag tgtgctcgtc atcgaaagtg ctcctacga gtcggacaga   180
ggtcctatca ttgaggacct gaacgcctac ggcgacatct tggcagcag tgtagaccac   240
gcctacgaga ccgtggagct cgctaccaac aatcaaaccg cgctggtgcg ctccggaaat   300
ggtctcggtg gctctactct aatcaatggt ggcacctgga ctcgccccca caaggcacag   360
gttgactctt gggagactgt ctttggaaat gagggctgga actgggacaa tgtggccgcc   420
tactccctcc aggctgagcg tgctcgcgca ccaaatgcca acagatcgc tgctggccac   480
tacttcaaca cctcctgcca tggtgttaat ggtactgtcc atgccggacc ccgcgacacc   540
ggcgatgact attctcccat cgtcaaggct ctcatgagcg ctgtcgaaga ccggggcgtt   600
cccaccaaga aagacttcgg atgcggtgac ccccatggtg tgtccatgtt ccccaacacc   660
ttgcacgaag accaagtgcg ctccgatgcc gctcgcgaat ggctacttcc caactaccaa   720
cgtcccaacc tgcaagtcct gaccggacag tattgcggta aggtgctcct tagccagaac   780
ggcaccaccc ctcgtgccgt tggcgtggaa ttcggcaccc acaagggcaa caccaacaac   840
gtttacgcta agcacgaggt cctcctggcc gcgggctccg ctgtctctcc acaatcctc    900
gaatattccg gtatcggaat gaagtccatc ctggagcccc ttggtatcga caccgtcgtt   960
```

-continued

```
gacctgcccg tcggcttgaa cctgcaggac cagaccaccg ctaccgtccg ctcccgcatc    1020
acctctgctg gtgcaggaca gggacaggcc gcttggttcg ccaccttcaa cgagaccttt    1080
ggtgactatt ccgaaaaggc acacgagctg ctcaacacca agctggagca gtgggccgaa    1140
gaggccgtcg cccgtggcgg attccacaac accaccgcct tgctcatcca gtacgagaac    1200
taccgcgact ggattgtcaa ccacaacgtc gcgtactcgg aactcttcct cgacactgcc    1260
ggagtagcca gcttcgatgt gtgggacctt ctgcccttca cccgaggata cgttcacatc    1320
ctcgacaagg accctacct tcaccacttc gcctacgacc tcagtactt cctcaacgag     1380 ctggacctgc tcggtcaggc tgccgctact caactggccc gcaacatctc caactccggt    1440
gccatgcaga cctacttcgc tggggagact atccccggtg ataacctcgc gtatgatgcc    1500
gatttgagcg cctggactga gtacatcccg taccacttcc gtcctaacta ccatggcgtg    1560
ggtacttgct ccatgatgcc gaaggagatg ggcggtgttg ttgataatgc tgcccgtgtg    1620
tatggtgtgc agggactgcg tgtcattgat ggttctattc ctcctacgca aatgtcgtcc    1680
catgtcatga cggtgttcta tgccatggcg ctaaaaattt cggatgctat cttggaagat    1740
tatgcttcca tgcagtgaga ggaaga                                         1766
```

<210> SEQ ID NO 19
<211> LENGTH: 583
<212> TYPE: PRT
<213> ORGANISM: Artificial Sequence
<220> FEATURE:
<223> OTHER INFORMATION: F19-B

<400> SEQUENCE: 19

```
Ser Asn Gly Ile Glu Ala Ser Leu Leu Thr Asp Pro Lys Asp Val Ser
1               5                   10                  15

Gly Arg Thr Val Asp Tyr Ile Ile Cys Gly Gly Gly Leu Val Gly Leu
                20                  25                  30

Thr Thr Ala Ala Lys Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Ile Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Thr Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220
```

```
Arg Ser Asp Ala Ala Arg Glu Trp Leu Leu Pro Asn Tyr Gln Arg Pro
225                 230                 235                 240

Asn Leu Gln Val Leu Thr Gly Gln Tyr Cys Gly Lys Val Leu Leu Ser
            245                 250                 255

Gln Asn Gly Thr Thr Pro Arg Ala Val Gly Val Glu Phe Gly Thr His
        260                 265                 270

Lys Gly Asn Thr His Asn Val Tyr Ala Lys His Glu Val Leu Leu Ala
    275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580
```

<210> SEQ ID NO 20
<211> LENGTH: 1766
<212> TYPE: DNA
<213> ORGANISM: Artificial Sequence
<220> FEATURE:
<223> OTHER INFORMATION: GOD-M5-A

<400> SEQUENCE: 20

-continued

```
gaattcagca atggaattga agcaagcctc ctgactgacc ccaaggaggt tgccggccgc      60
actgtcgact acatcatcgc tggtggaggt ctgactggac tcaccgtcgc tgcccgtctg     120
acggagaacc ccgatatcac tgtgcttgtc atcgaaagtg gctgctacga gtctgacaga     180
ggtcctatca ttgaggacct gaacgcttac ggtgacattt ttggcagcag tgtggaccac     240
gcctacgaga ctgtctgcct cgccaccaac aatcagactg cgctgatccg ctccggaaat     300
ggtctcggtg gctctaccct cgtcaacggt ggcacctgga ctcgccccca caaggcacaa     360
gttgactcat gggagaccgt cttcggaaat gagggctgga actgggacag cgtggccgcc     420
tactccctcc aggctgagcg tgctcgcgca ccaaatgcca acagattgc tgctggccac      480
tactttaatg catcctgcca tggtatcaat ggtactgtcc acgccggacc ccgcgatacc     540
ggtgatgact actcccccat cgtcaaggct ctcatgagcg ctgtcgaaga caggggcgtt     600
cccaccaaga aggacttggg atgcggtgac ccccatggtg tgtccatgtt ccccaacacc     660
ttgcacgaag accaagtgcg ctctgatgcc gctcgcgaat ggctcctccc caactaccag     720
cgtcccaacc tgcaagtcct ctgcggacag tatgttggaa aggtcctgct cagccagaac     780
gctaccacac ctcgtgccgt tggcgtggaa ttcggcaccc acaagggcaa cacccacaac     840
gtctacgcta agcacgaggt cctcctggcc gctggatccg ctgtctctcc caccatcctc     900
gaatattccg gtatcggaat gaagtccatt ctagagcctc ttggaattaa gaccgtcgtt     960
gacctgcccg ttggtctcaa ccttcaggac cagaccacct ctaccgtccg ctcacgcatt    1020
acctccgccg gtgccggaca gggacaggcc gcttggttcg ctaccttcaa cgagaccttt    1080
ggcgactaca ccgaaaaggc tcacgagctg ctcaacacca agctggagca gtgggccgaa    1140
gaggccgtcg cccgtggcgg attccacaac accaccgctt tgctcatcca gtacgagaac    1200
taccgcgact ggatcgtcaa ggacaatgtc gcatactcgg aactcttcct cgacacggcc    1260
ggagaagcca gtttcgatgt gtgggatctt ctgcccttca ctagaggata cgtccacatc    1320
ctcgacaagg accctacct ccgccatttc gcctacgacc tcagtactt cctcaacgag      1380
cttgacctgc tcggccaggc tgccgccact cagctggccc gcaacatctc taactccggt    1440
gccatgcaaa cttatttcgc tggagagact attcccggtg acaacctcgc gtatgatgcc    1500
gacttgagag cctgggttga gtatatcccg taccacttcc gccctaacta ccatggtgtg    1560
ggtacttgct ccatgatgcc gaaggagatg gcgtgttg tcgacaatgc tgcccgtgtg      1620
tatggtgtgc agggactgcg agtcatcgat ggttctattc cccctacgca gatgtcgtcc    1680
catgttatga cggtcttta tgccatggcc ttaaagattg cggatgccgt cttggcggat    1740
tacgcttcta tgcagtaaga ggaaga                                         1766
```

<210> SEQ ID NO 21
<211> LENGTH: 583
<212> TYPE: PRT
<213> ORGANISM: Artificial Sequence
<220> FEATURE:
<223> OTHER INFORMATION: GOD-M5-A

<400> SEQUENCE: 21

Ser Asn Gly Ile Glu Ala Ser Leu Leu Thr Asp Pro Lys Glu Val Ala
1               5                   10                  15

Gly Arg Thr Val Asp Tyr Ile Ile Ala Gly Gly Leu Thr Gly Leu
            20                  25                  30

Thr Val Ala Ala Arg Leu Thr Glu Asn Pro Asp Ile Thr Val Leu Val
        35                  40                  45

```
Ile Glu Ser Gly Cys Tyr Glu Ser Asp Arg Gly Pro Ile Glu Asp
 50                  55                  60

Leu Asn Ala Tyr Gly Asp Ile Phe Gly Ser Ser Val Asp His Ala Tyr
 65                  70                  75                  80

Glu Thr Val Cys Leu Ala Thr Asn Asn Gln Thr Ala Leu Ile Arg Ser
                 85                  90                  95

Gly Asn Gly Leu Gly Gly Ser Thr Leu Val Asn Gly Gly Thr Trp Thr
                100                 105                 110

Arg Pro His Lys Ala Gln Val Asp Ser Trp Glu Thr Val Phe Gly Asn
                115                 120                 125

Glu Gly Trp Asn Trp Asp Ser Val Ala Ala Tyr Ser Leu Gln Ala Glu
        130                 135                 140

Arg Ala Arg Ala Pro Asn Ala Lys Gln Ile Ala Ala Gly His Tyr Phe
145                 150                 155                 160

Asn Ala Ser Cys His Gly Ile Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Leu Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Cys Gly Gln Tyr Val Gly Lys Val Leu Leu Ser
                245                 250                 255

Gln Asn Ala Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Lys Thr Val Val Asp Leu
305                 310                 315                 320

Pro Val Gly Leu Asn Leu Gln Asp Gln Thr Thr Ser Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Thr Glu Lys Ala His Glu Leu
        355                 360                 365

Leu Asn Thr Lys Leu Glu Gln Trp Ala Glu Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Lys Asp Asn Val Ala Tyr Ser Glu Leu Phe Leu Asp
                405                 410                 415

Thr Ala Gly Glu Ala Ser Phe Asp Val Trp Asp Leu Leu Pro Phe Thr
            420                 425                 430

Arg Gly Tyr Val His Ile Leu Asp Lys Asp Pro Tyr Leu Arg His Phe
        435                 440                 445

Ala Tyr Asp Pro Gln Tyr Phe Leu Asn Glu Leu Asp Leu Leu Gly Gln
    450                 455                 460
```

```
Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Arg Ala Trp Val Glu Tyr Ile Pro Tyr His Phe Arg
            500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
        530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ala Asp Ala Val Leu
            565                 570                 575

Ala Asp Tyr Ala Ser Met Gln
            580

<210> SEQ ID NO 22
<211> LENGTH: 1766
<212> TYPE: DNA
<213> ORGANISM: Artificial Sequence
<220> FEATURE:
<223> OTHER INFORMATION: GOD-M5-B

<400> SEQUENCE: 22
gaattcagca atggaattga agcaagcctc ctgactgacc ccaaggaggt tgccggccgc      60
actgtcgact acatcatctg cggtggaggt ctgactggac tcaccgtcgc tgcccgtctg     120
acggagaacc ccgatatcac tgtgcttgtc atcgaaagtg gctcctacga gtctgacaga     180
ggtcctatca ttgaggacct gaacgcttac ggtgacattt ttggcagcag tgtgaccac      240
gcctacgaga ctgtctgcct cgccaccaac aatcagactg cgctgatccg ctccggaaat     300
ggtctcggtg gctctaccct cgtcaacggt ggcacctgga ctcgccccca caaggcacaa     360
gttgactcat gggagaccgt cttcggaaat gagggctgga actgggacag cgtggccgcc     420
tactccctcc aggctgagcg tgctcgcgca ccaaatgcca acagattgc tgctggccac     480
tactttaatg catcctgcca tggtatcaat ggtactgtcc acgccggacc ccgcgatacc     540
ggtgatgact actcccccat cgtcaaggct ctcatgagcg ctgtcgaaga cagggggcgtt     600
cccaccaaga aggacttggg atgcggtgac ccccatggtg tgtccatgtt ccccaacacc     660
ttgcacgaag accaagtgcg ctctgatgcc gctcgcgaat ggctcctccc caactaccag     720
cgtcccaacc tgcaagtcct cactggacag tattgcggaa aggtcctgct cagccagaac     780
gctaccacac tcgtgccgt tggcgtggaa ttcggcaccc acaagggcaa cacccacaac     840
gtctacgcta agcacgaggt cctcctggcc gctggatccg ctgtctctcc caccatcctc     900
gaatattccg gtatcggaat gaagtccatt ctagagcctc ttggaattaa gaccgtcgtt     960
gacctgcccg ttggtctcaa ccttcaggac cagaccacct ctaccgtccg ctcacgcatt    1020
acctccgccg gtgccggaca gggacaggcc gcttggttcg ctaccttcaa cgagaccttt    1080
ggcgactaca ccgaaaaggc tcacgagctg ctcaacacca agctggagca gtgggccgaa    1140
gaggccgtcg cccgtggcgg attccacaac accaccgctt gctcatcca gtacgagaac    1200
taccgcgact ggatcgtcaa ggacaatgtc gcatactcgg aactcttcct cgacacggcc    1260
ggagaagcca gtttcgatgt gtgggatctt ctgcccttca ctagaggata cgtccacatc    1320
ctcgacaagg acccctacct ccgccatttc gcctacgacc ctcagtactt cctcaacgag    1380
```

```
cttgacctgc tcggccaggc tgccgccact cagctggccc gcaacatctc taactccggt   1440
gccatgcaaa cttatttcgc tggagagact attcccggtg acaacctcgc gtatgatgcc   1500
gacttgagag cctgggttga gtatatcccg taccacttcc gccctaacta ccatggtgtg   1560
ggtacttgct ccatgatgcc gaaggagatg ggcggtgttg tcgacaatgc tgcccgtgtg   1620
tatggtgtgc agggactgcg agtcatcgat ggttctattc cccctacgca gatgtcgtcc   1680
catgttatga cggtctttta tgccatggcc ttaaagattg cggatgccgt cttggcggat   1740
tacgcttcta tgcagtaaga ggaaga                                       1766
```

<210> SEQ ID NO 23
<211> LENGTH: 583
<212> TYPE: PRT
<213> ORGANISM: Artificial Sequence
<220> FEATURE:
<223> OTHER INFORMATION: GOD-M5-B

<400> SEQUENCE: 23

```
Ser Asn Gly Ile Glu Ala Ser Leu Leu Thr Asp Pro Lys Glu Val Ala
1               5                   10                  15

Gly Arg Thr Val Asp Tyr Ile Ile Cys Gly Gly Gly Leu Thr Gly Leu
            20                  25                  30

Thr Val Ala Ala Arg Leu Thr Glu Asn Pro Asp Ile Thr Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Cys Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Ser Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Ile Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Leu Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Cys Gly Lys Val Leu Leu Ser
                245                 250                 255

Gln Asn Ala Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285
```

```
Ala Gly Ser Ala Val Ser Pro Thr Ile Leu Glu Tyr Ser Gly Ile Gly
    290             295                 300
Met Lys Ser Ile Leu Glu Pro Leu Gly Ile Lys Thr Val Val Asp Leu
305             310                 315                 320
Pro Val Gly Leu Asn Leu Gln Asp Gln Thr Thr Ser Thr Val Arg Ser
            325                 330                 335
Arg Ile Thr Ser Ala Gly Ala Gly Gln Gly Gln Ala Ala Trp Phe Ala
            340             345                 350
Thr Phe Asn Glu Thr Phe Gly Asp Tyr Thr Glu Lys Ala His Glu Leu
        355             360                 365
Leu Asn Thr Lys Leu Glu Gln Trp Ala Glu Gly Ala Val Ala Arg Gly
    370             375                 380
Gly Phe His Asn Thr Thr Ala Leu Leu Ile Gln Tyr Glu Asn Tyr Arg
385             390                 395                 400
Asp Trp Ile Val Lys Asp Asn Val Ala Tyr Ser Glu Leu Phe Leu Asp
            405                 410                 415
Thr Ala Gly Glu Ala Ser Phe Asp Val Trp Asp Leu Leu Pro Phe Thr
            420             425                 430
Arg Gly Tyr Val His Ile Leu Asp Lys Asp Pro Tyr Leu Arg His Phe
            435                 440                 445
Ala Tyr Asp Pro Gln Tyr Phe Leu Asn Glu Leu Asp Leu Leu Gly Gln
    450             455                 460
Ala Ala Ala Thr Gln Leu Ala Arg Asn Ile Ser Asn Ser Gly Ala Met
465             470                 475                 480
Gln Thr Tyr Phe Ala Gly Glu Thr Ile Pro Gly Asp Asn Leu Ala Tyr
            485                 490                 495
Asp Ala Asp Leu Arg Ala Trp Val Glu Tyr Ile Pro Tyr His Phe Arg
            500                 505                 510
Pro Asn Tyr His Gly Val Gly Thr Cys Ser Met Met Pro Lys Glu Met
        515             520                 525
Gly Gly Val Val Asp Asn Ala Ala Arg Val Tyr Gly Val Gln Gly Leu
    530             535                 540
Arg Val Ile Asp Gly Ser Ile Pro Pro Thr Gln Met Ser Ser His Val
545             550                 555                 560
Met Thr Val Phe Tyr Ala Met Ala Leu Lys Ile Ala Asp Ala Val Leu
            565                 570                 575
Ala Asp Tyr Ala Ser Met Gln
            580
```